United States Patent
Chou et al.

(10) Patent No.: US 11,512,302 B2
(45) Date of Patent: Nov. 29, 2022

(54) MODIFICATIONS TO LYSINE DECARBOXYLASE ENZYMES

(71) Applicants: CATHAY BIOTECH INC., Shanghai (CN); CIBT America Inc., Newark, DE (US)

(72) Inventors: Howard Chou, Shanghai (CN); Wenqiang Lu, Shanghai (CN); Ling Chen, Shanghai (CN); Lijun Yu, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 96 days.

(21) Appl. No.: 16/614,265

(22) PCT Filed: May 16, 2017

(86) PCT No.: PCT/CN2017/084540
§ 371 (c)(1),
(2) Date: Nov. 15, 2019

(87) PCT Pub. No.: WO2018/209563
PCT Pub. Date: Nov. 22, 2018

(65) Prior Publication Data
US 2021/0155962 A1 May 27, 2021

(51) Int. Cl.
*C12N 9/88* (2006.01)
*C12P 13/00* (2006.01)
*C12N 15/70* (2006.01)
*C12N 15/77* (2006.01)

(52) U.S. Cl.
CPC ............... *C12N 9/88* (2013.01); *C12N 15/70* (2013.01); *C12N 15/77* (2013.01); *C12P 13/001* (2013.01); *C12Y 401/01018* (2013.01)

(58) Field of Classification Search
CPC ................................ C12N 9/88; C12P 13/001
See application file for complete search history.

(56) References Cited

U.S. PATENT DOCUMENTS

| | | | |
|---|---|---|---|
| 2015/0132808 A1 | 5/2015 | Mochizuki et al. | |
| 2016/0376580 A1 | 12/2016 | Oonishi et al. | |
| 2018/0291362 A1 | 10/2018 | Kim et al. | |

FOREIGN PATENT DOCUMENTS

| | | |
|---|---|---|
| CN | 103789292 A | 5/2014 |
| CN | 104762336 | 7/2015 |
| WO | WO-2016119230 | 8/2016 |
| WO | WO-2017022944 | 2/2017 |

OTHER PUBLICATIONS

Studer. Residue mutations and their impact on protein structure and function: detecting beneficial and pathogenic changes. Biochem. J. (2013) 449, 581-594.*
Flecker. Cloning and characterization of a lysine decarboxylase gene from Hafnia alvei.Mol. Gen. Genet. 203, 177-184, 1986.*
Heidelberg. Q9KV75_VIBCH. UniProtKB/TrEMBL Database. Mar. 16, 2016.*
"lysine decarboxylase CadA [*Escherichia coli*]. Accession No. WP_044698312.1." NCBI Reference Sequence., Mar. 6, 2015.
"unnamed protein product [Hafnia alvei]. Accession No. CAV25914.1" *NCBI GenBank.*, Dec. 17, 2008.
"unnamed protein product [Vibrio parahaemolyticus]. Accession No. CBG14132.1." *NCBI GenBank.*, Sep. 25, 2009.
"unnamed protein product [*Salmonella enterica* subsp. *enterica* serovar Typhimurium*], Accession No. CBE70874.1."*NCBI GenBank.*, Sep. 18, 2009.
Extended European Search Report for Application No. EP 17910224.9, dated Dec. 21, 2020.
Seo, Hyung-Min et al., "In situ immobilization of lysine decarboxylase on a biopolymer by fusion with phasin Immobilization of CadA on intracellular PHA", *Process Biochemistry*, vol. 51, No. 10, pp. 1413-1419 (2016).
Kou, Fengyu et al., "Characterization of a new lysine decarboxylase from *Aliivibrio salmonicida* for cadaverine production at alkaline pH", *Journal of Molecular Catalysis B: Enzymatic*, vol. 133, pp. S88-S94 (2016).
International Search Report for Application No. PCT/CN2017/084540, dated Feb. 8, 2018.

* cited by examiner

*Primary Examiner* — Yong D Pak
(74) *Attorney, Agent, or Firm* — Marshall, Gerstein & Borun LLP

(57) ABSTRACT

The invention provides CadA polypeptides with mutations that increase activity in alkaline pH compared to the wild-type lysine decarboxylase. The invention also provides methods of generating such mutant polypeptides, microorganisms genetically modified to overexpress the mutant polypeptides, and methods of generating such microorganism.

17 Claims, 2 Drawing Sheets
Specification includes a Sequence Listing.

| | |
|---|---|
| SALMONELLA_ENTERICA_WP_001540636.1 (SEQ ID NO: 5) | MNVIAIMNHMGVYFKEEPIRELHRALEGLNFRIVYPNDREDLLKLIENNSRLCGVIFDWD |
| ESCHERICHIA_MULTISPECIES_CADA (SEQ ID NO: 2) | MNVIAILNHMGVYFKEEPIRELHRALERLNFQIVYPNDRDDLLKLIENNARLCGVIFDWD |
| KLEBSIELLA_MULTISPECIES_WP_012968785 (SEQ ID NO: 3) | MNVIAIMNHMGVYFKEEPIRELHRALERLDFRIVYPNDRDDLLKLIENNSRLCGVIFDWD |
| ENTEROBACTERIAECEAE_MULTISPECIES_WP_002892486.1 (SEQ ID NO: 4) | MNVIAIMNHMGVYFKEEPIRELHRALERLDFRIVYPNDRDDLLKLIENNSRLCGVIFDWD |
| | ****:***************:*:**:*:*************** |
| SALMONELLA_ENTERICA_WP_001540636.1 | KYNLELCEEISKLNEYMPLYAFANSYSTLDVSLNDLRMQVRFFEYALGAATDIAAKIRQN |
| ESCHERICHIA_MULTISPECIES_CADA | KYNLELCEEISKMNENLPLYAFANTYSTLDVSLNDLRLQISFFEYALGAAEDIANKIKQT |
| KLEBSIELLA_MULTISPECIES_WP_012968785 | KYNLELCEEISKMNEYMPLYAFANTYSTLDVSLNDLRMQVRFFEYALGAAEDIANKIKQN |
| ENTEROBACTERIAECEAE_MULTISPECIES_WP_002892486.1 | KYNLELCEEISKMNEYMPLYAFANTYSTLDVSLNDLRMQVRFFEYALGAAEDIANKIKQN |
| | **********::*******:*******:*:********:*:****: . |
| SALMONELLA_ENTERICA_WP_001540636.1 | TDEYIDNILPPLTKALFKYVREGKYTFCTPGHMGGTAFQKSPVGSIFYDFFGPNTMKSDI |
| ESCHERICHIA_MULTISPECIES_CADA | TDEYINTILPPLTKALFKYVREGKYTFCTPGHMGGTAFQKSPVGSLFYDFFGPNTMKSDI |
| KLEBSIELLA_MULTISPECIES_WP_012968785 | TDEYIDTILPPLTKALFKYVREGKYTFCTPGHMGGTAFQKSPVGSIFYDFFGPNTMKSDI |
| ENTEROBACTERIAECEAE_MULTISPECIES_WP_002892486.1 | TDEYIDTILPPLTKALFKYVREGKYTFCTPGHMGGTAFQKSPVGSIFYDFFGSNTMKSDI |
| | ***: .***************************:****.***** |
| SALMONELLA_ENTERICA_WP_001540636.1 | SISVSELGSLLDHSGPHKEAEEYIARVFNAERSYMVTNGTSTANKIVGMYSAPAGSTVLI |
| ESCHERICHIA_MULTISPECIES_CADA | SISVSELGSLLDHSGPHKEAEQYIARVFNADRSYMVTNGTSTANKIVGMYSAPAGSTILI |
| KLEBSIELLA_MULTISPECIES_WP_012968785 | SISVSELGSLLDHSGPHKEAEEYIARVFNAERSYMVTNGTSTANKIVGMYSAPAGSTVLI |
| ENTEROBACTERIAECEAE_MULTISPECIES_WP_002892486.1 | SISVSELGSLLDHSGPHKEAEEYIARVFNAERSYMVTNGTSTANKIVGMYSAPAGSTVLI |
| | *******************:***:*********************: |
| SALMONELLA_ENTERICA_WP_001540636.1 | DRNCHKSLTHLMMMSDITPIYFRPTRNAYGILGGIPQSEFQHATIAKRVKETPNATWPVH |
| ESCHERICHIA_MULTISPECIES_CADA | DRNCHKSLTHLMMMSDVTPIYFRPTRNAYGILGGIPQSEFQHATIAKRVKETPNATWPVH |
| KLEBSIELLA_MULTISPECIES_WP_012968785 | DRNCHKSLTHLMMMSDITPIYFRPTRNAYGILGGIPQSEFQHATIAKRVKETPNATWPVH |
| ENTEROBACTERIAECEAE_MULTISPECIES_WP_002892486.1 | DRNCHKSLTHLMMMSDITPIYFRPTRNAYGILGGIPQSEFQHATIAKRVKETPNATWPVH |
| | **************:***************************************** |
| SALMONELLA_ENTERICA_WP_001540636.1 | AVITNSTYDGLLYNTDYIKKTLDVKSIHFDSAWVPYTNFSPIYQGKCGMSGDRVEGKIIY |
| ESCHERICHIA_MULTISPECIES_CADA | AVITNSTYDGLLYNTDFIKKTLDVKSIHFDSAWVPYTNFSPIYEGKCGMSGGRVEGKVIY |
| KLEBSIELLA_MULTISPECIES_WP_012968785 | AVITNSTYDGLLYNTDFIKKTLDVKSIHFDSAWVPYTNFSPIYEGKCGMSGGRVEGKVIY |
| ENTEROBACTERIAECEAE_MULTISPECIES_WP_002892486.1 | AVITNSTYDGLLYNTDFIKKTLDVKSIHFDSAWVPYTNFSPIYEGKCGMSGGRVEGKVIY |
| | **************:*********************:***.*: |

```
SALMONELLA_ENTERICA_WP_001540636.1          ETQSTHKLLAAFSQASMIHVKGDINEETFNEAYMMHTTTSPHYGIVASTETAAAMMKGNA
ESCHERICHIA_MULTISPECIES_CADA               ETQSTHKLLAAFSQASMIHVKGDINEETFNEAYMMHTTTSPHYGIVASTETAAAMMKGNA
KLEBSIELLA_MULTISPECIES_WP_012968785        ETQSTHKLLAAFSQASMIHVKGDVNEETFNEAYMMHTTTSPHYGIVASTETAAAMMKGNA
ENTEROBACTERIAECEAE_MULTISPECIES_WP_002892486.1  ETQSTHKLLAAFSQASMIHVKGDVNEETFNEAYMMHTTTSPHYGIVASTETAAAMMKGNA
                                            ****************************:*******************************

SALMONELLA_ENTERICA_WP_001540636.1          GKRLINGSIERAIKFRKEIKRLKSESDGWFFDVWQPEHIDGAECWPLRSDSAWHGFKNID
ESCHERICHIA_MULTISPECIES_CADA               GKRLINGSIERAIKFRKEIKRLRTESDGWFFDVWQPDHIDTTECWPLRSDSTWHGFKNID
KLEBSIELLA_MULTISPECIES_WP_012968785        GKRLIDGSIERSIKFRKEIKRLKGESDGWFFDVWQPEHIDGPECWPLRSDSAWHGFKNID
ENTEROBACTERIAECEAE_MULTISPECIES_WP_002892486.1  GKRLIDGSIERSIKFRKEIKRLKGESDGWFFDVWQPEHIDGPECWPLRSDSAWHGFKNID
                                            ****:.*****:**********: :******************.*:***:.********

SALMONELLA_ENTERICA_WP_001540636.1          NEHMYLDPIKVTLLTPGMKKDGTMDEFGIPASLVAKYLDERGIIVEKTGPYNLLFLFSIG
ESCHERICHIA_MULTISPECIES_CADA               NEHMYLDPIKVTLLTPGMEKDGTMSDFGIPASIVAKYLDEHGIVEKTGPYNLLFLFSIG
KLEBSIELLA_MULTISPECIES_WP_012968785        NEHMYLDPIKVTLLTPGMKKDGTMDDFGIPASIVAKYLDEHGIVEKTGPYNLLFLFSIG
ENTEROBACTERIAECEAE_MULTISPECIES_WP_002892486.1  NEHMYLDPIKVTLLTPGMKKDGTMDDFGIPASIVAKYLDEHGIVEKTGPYNLLFLFSIG
                                            ******************:*****.******:*******:**:***************

SALMONELLA_ENTERICA_WP_001540636.1          IDKTKALSLLRALTEFKRAFDLNLRVKNILPALYREAPEFYENMRIQELAQNIHKLVEHH
ESCHERICHIA_MULTISPECIES_CADA               IDKTKALSLLRALTDFKRAFDLNLRVKNMLPSLYREDPEFYENMRIQELAQNIHKLIVHH
KLEBSIELLA_MULTISPECIES_WP_012968785        IDKTKALSLLRALTDFKRAFDLNLRVKNMLPSLYREDPEFYENMRIQDLAQNIHKLIEHH
ENTEROBACTERIAECEAE_MULTISPECIES_WP_002892486.1  IDKTKALSLLRALTDFKRAFDLNLRVKNMLPSLYREDPEFYENMRIQDLAQNIHKLIEHH
                                            **************:*************:**:*** **********::*********: **

SALMONELLA_ENTERICA_WP_001540636.1          NLPDLMYRAFEVLPKMVMTPYTAFQKELHGETEEVYLEEMVGRVNANMILPYPPGVPLVM
ESCHERICHIA_MULTISPECIES_CADA               NLPDLMYRAFEVLPTMVMTPYAAFQKELHGMTEEVYLDEMVGRINANMILPYPPGVPLVM
KLEBSIELLA_MULTISPECIES_WP_012968785        NLPDLMFRAFEVLPSMVMTPYAAFQKELHGQTEEVYLEEMVGRVNANMILPYPPGVPLVM
ENTEROBACTERIAECEAE_MULTISPECIES_WP_002892486.1  NLPDLMFRAFEVLPSMVMTPYAAFQKELHGQTEEVYLEEMVGRVNANMILPYPPGVPLVM
                                            ******:*******.******:*******  *****:*****:****************

SALMONELLA_ENTERICA_WP_001540636.1          PGEMITEESRPVLEFLQMLCEIGAHYPGFETDIHGAYRQADGRYTVKVLKENTK---
ESCHERICHIA_MULTISPECIES_CADA               PGEMITEESRPVLEFLQMLCEIGAHYPGFETDIHGAYRQADGRYTVKVLKEESKK*
KLEBSIELLA_MULTISPECIES_WP_012968785        PGEMITEESRPVLEFLQMLCEIGAHYPGFETDIHGAYRQADGRYTVKVLKEENNK--
ENTEROBACTERIAECEAE_MULTISPECIES_WP_002892486.1  PGEMITEESRPVLEFLQMLCEIGAHYPGFETDIHGAYRQADGRYTVKVLKEENNK--
                                            **************************************************:.:
``` con't

MODIFICATIONS TO LYSINE DECARBOXYLASE ENZYMES

BACKGROUND OF THE INVENTION

Most enzymes function optimally within a narrow pH range, because they are amphoteric molecules. The pH of the surrounding environment directly affects the charges on the acidic and basic groups of the amino acids that make up the enzyme. These changes in charge affect the net charge of the enzyme, the pKa of the active site, and the charge distribution across the surface of the enzyme. As a result, changes in pH can affect the activity, solubility, and stability of an enzyme.

The class of proteins known as acid decarboxylases is a group of enzymes that catalyze the decarboxylase reaction of basic amino acids (e.g., lysine, arginine, ornithine) in order to generate polyamines as part of the acid stress response in many microorganisms. Escherichia coli has several PLP-dependent acid decarboxylases: CadA, LdcC, AdiA, SpeA, SpeC, SpeF, GadA, and GadB. All of these enzymes function within a narrow pH range, and the enzyme activity decreases significantly outside of that pH range (Kanjee et al., Biochemistry 50, 9388-9398, 2011). It has been previously observed that these PLP-dependent decarboxylases dimerize in order to form a complete active site. In some cases, such as CadA, the dimers form decamers that aggregate into higher molecular weight protein complexes required for optimal function. The inhibition of higher molecular weight protein complex formation (e.g., in conditions outside of the optimal pH) leads to a significant decrease in function (Kanjee et al., *The EMBO Journal* 30, 931-944, 2011).

The pKa values of individual amino acids in a protein are important for determining its biomolecular function, because one of the dominant reactions in a protein-water solution is the exchange of protons by certain amino acids with the environment of the protein. The pKa is a measure of the difference in free energy between the neutral and charged states, and indicates the propensity of an amino acid to donate or accept a proton. Certain amino acids have titratable groups that make them more amenable to accept and donate protons. These amino acids include aspartate, glutamate, cysteine, serine, tyrosine, threonine, histidine, lysine, and arginine. Illustrative pKa values of some amino acids are: aspartate is 4.0, glutamate is 4.4, cysteine is 8.7, tyrosine is 9.6, histidine is 6.3, lysine is 10.4, and arginine is 13.0 (Nielsen JE & Vriend G, *Proteins* 43, 403-412, 2001). These pKa values can vary by 0.5, depending on the literature source.

Whether a titratable group accepts or donates a proton will depend on its environment, such as the pH or other amino acids in its proximity. For example, when the pH is less than the pKa of the titratable group, then the group will more likely accept a proton. Conversely, when the pH is greater than the pKa of the titratable group, then the group will more likely donate a proton. When a titratable group of an amino acid either accepts or donates a proton, the amino acid can become either positively charged, negatively charged, or neutral depending on the charge it started with before the proton exchange happened. Charged groups can interact with other charged groups when the two groups are brought into proximity of one another. Like charges repel each other and opposite charges attract each other. Neutrally charged groups that are protonated can still interact with other groups through hydrogen bond interactions.

An understanding of the pKa values of the titratable groups of a protein is not only important for understanding how pH affects polypeptide folding and enzyme activity, but also protein-protein interactions (Jensen, *Curr Pharm Biotechnol* 9, 96-102, 2008), especially in the cases of the acid decarboxylases that undergo significant changes in their quaternary structure as a result of a change in the pH of the environment. There have been few studies in evaluating the effect of mutations at various amino acids with titratable groups on the function of the acid decarboxylases.

Based on prior literature (Kanjee, et al. *The EMBO Journal* 30, 931-944, 2011), CadA transitions from a state that consists of decamers and high-order oligomers to a state that is composed mostly of dimers when the pH of the environment changes. The formation of decamers is a prerequisite for the formation of high-order oligomers. It has been shown that CadA functions optimally at a pH of 5.0-5.5 (Lemonnier & Lane, *Microbiology* 144, 751-760, 1998). At this acidic pH, Kanjee et al. show using EM that CadA exists mainly as high-order oligomers. When the pH is increased above 6.0 or when the inhibitor ppGpp is present, the high-order oligomers do not form and decarboxylase function is significantly reduced. However, there is an absence of literature that describes how the CadA high-order oligomers form and the amino acid residues that play a role in their formation.

BRIEF SUMMARY OF ASPECTS OF THE DISCLOSURE

This invention is based, in part, on the discovery of mutations that provide the ability to stabilize the chemical interactions necessary for quaternary structure formation, and increase stability to allow a mutant acid decarboxylase protein to function across a wider pH range. The ability to function across a wider pH range is important in maintaining a high reaction rate without the need to add additional chemicals to maintain pH. The maintenance of a high reaction rate across a wide pH range would enable lysine to be converted into cadaverine faster and reduce the amount of utilities required. The tolerance of the protein for alkaline pH eliminates the need to add additional chemicals to maintain pH. These chemicals used to maintain pH oftentimes form salts (e.g., $SO_4^{2-}$ or $Cl^-$) that go either into the wastewater or must be removed from the process using additional purification steps. Therefore, a mutant acid decarboxylase that functions at a wider pH range than wild-type would decrease the cost and the environmental footprint of the overall process by reducing the amount of salts formed during the process.

In one aspect, the invention thus provides a CadA variant polypeptide comprising at least one amino acid substitution at a lysine residue in a region corresponding to amino acids 276 to 509 as determined with reference to SEQ ID NO:2, where the lysine residue occurs at the surface of the protein with the side chain oriented towards the external environment in a segment of the protein that lacks a defined secondary structure; and wherein the CadA variant polypeptide has at least 70% identity to any one of SEQ ID NOS:2 to 5. In some embodiments, a CadA variant polypeptide comprises at least one amino acid substitution at a lysine residue in a region corresponding to amino acids 314-326, the region between β11 and α12 that includes β12, as determined with reference to SEQ ID NO:2; and wherein the CadA variant polypeptide has at least 70% identity to any one of SEQ ID NOS:2 to 5. In some embodiments, the substitution is at a lysine residue at position 320 or position 325 as determined with reference to SEQ ID NO:2. In some embodiments, both positions 320 and 325 are substituted relative to SEQ ID NO:2. In some embodiment; the substitution at position 320 is K320A/C/E/G/H/I/L/M/S/V/Y. In some embodiments, the substitution is K320C/E/G/L/V/Y.

In some embodiments, a CadA variant polypeptide having a substitution at a lysine residue further comprises at least one amino acid substitution at a glutamic acid residue in a region corresponding to amino acids 276 to 509 as determined with reference to SEQ ID NO:2, where the glutamic acid residue occurs at the surface of the protein with the side chain oriented towards the external environment in a segment of the protein that lacks a defined secondary structure; and wherein the CadA variant polypeptide has at least 70% identity to any one of SEQ ID NOS:2 to 5. In some embodiments, the substitution is at a glutamic acid residue at a position selected from the group consisting of positions 291, 344, 355, 463, 482, and 499 as determined with reference to SEQ ID NO:2. In some embodiments, the amino acid substitution is E291A/C/D/H/R/V/G/K/N/S, E355C/F/H/K/L/M/N/P/Q/R/S/T/V/Y, or E482C/F/I/L/S/W/Y/A/H/K/M. In some embodiments, the amino acid substitution is E291A/C/D/H/R/V, E355C/F/H/K/L/M/N/P/Q/R/S/T/V/Y, or E482C/F/I/L/S/W/Y. In some embodiments a CadA variant polypeptide comprises substitutions of glutamic acid residues at at least two positions selected from the group consisting of positions 291, 344, 355, 463, 482, and 499. In some embodiments, a CadA variant polypeptide comprises substitutions of glutamic acid residues at at least three positions selected from the group consisting of positions 291, 344, 355, 463, 482, and 499. In some embodiments, a CadA variant polypeptide comprises substitutions of glutamic acid residues at four or five positions selected from the group consisting of positions 291, 344, 355, 463, 482, and 499; or at all six of the positions.

In some embodiments, a CadA variant polypeptide comprising a substitution at a lysine residue, or a substitution at a lysine residue and a glutamate, e.g., as described above in the preceding two paragraphs, has at least 70% identity to SEQ ID NO:2. In some embodiments, the CadA variant polypeptide has at least 75%, at least 80%, at least 85%, at least 90%, or at least 95% identity to SEQ ID NO:2. In some embodiments, a CadA variant polypeptide as described herein has at least 70% identity to SEQ ID NO:3, SEQ ID NO:4, or SEQ ID NO:5. In some embodiments, the CadA variant polypeptide has at least 75%, at least 80%, at least 85%, at least 90%, or at least 95% identity to SEQ ID NO:3, SEQ ID NO:4, or SEQ ID NO:5.

In a further aspect, the invention provides a genetically modified host cell comprising a CadA variant polypeptide as described herein, e.g., in the preceding paragraph. In typical embodiments, the genetically modified host cell is genetically modified to over express one or more lysine biosynthesis polypeptides. In some embodiments, the host cell is a bacterium. In further embodiments, the host cell is from the genus *Escherichia, Hafnia*, or *Corynebacteria*. In some embodiments, the genetically modified host cell is *Escherichia coli*. In some embodiments, the genetically modified host cell is Hafnia *alvei*. In some embodiments, the genetically modified host cell is *Corynebacterium glutamicum*.

In an additional aspect, the invention provides a polynucleotide comprising a nucleic acid sequence encoding a CadA variant polypeptide as described herein, e.g., in the preceding paragraphs in this section. In further aspects, the invention additionally provides an expression vector comprising a polynucleotide encoding the CadA variant, and/or a genetically modified host cell comprising the expression vector. In some embodiments, the host cell is a bacterium, e.g., from the genus *Escherichia, Hafnia*, or *Corynebacteria*. In some embodiments, the genetically modified host cell is *Escherichia coli*. In some embodiments, the genetically modified host cell is Hafnia *alvei*. In some embodiments, the genetically modified host cell is *Corynebacterium glutamicum*.

In a further aspect, the invention provides a genetically modified host cell comprising a polynucleotide that comprises a nucleic acid sequence encoding a CadA variant polypeptide as described herein, e.g., in the preceding paragraphs in this section, wherein the nucleic acid sequence encoding the CadA variant polypeptide is integrated into the host cell chromosome. In some embodiments, the host cell is a bacterium, e.g., from the genus *Escherichia, Hafnia*, or *Corynebacteria*. In some embodiments, the genetically modified host cell is *Escherichia coli*. In some embodiments, the genetically modified host cell is Hafnia *alvei*. In some embodiments, the genetically modified host cell is *Corynebacterium glutamicum*.

In another aspect, the invention provides a method of producing cadaverine, the method comprising culturing a genetically modified host cell as described herein, e.g., in the preceding paragraphs in this section, under conditions in which CadA variant polypeptide is expressed.

DESCRIPTION OF THE FIGURES

FIG. 1 shows an alignment of the *E. coli* CadA polypeptide sequence SEQ ID NO:2 with CadA homologs from *Salmonella enterica* (WP_001540636.1, SEQ ID NO: 5), *Klebsiella* multispecies (WP_012968785, SEQ ID NO: 3), and Enterobacteriaeceae multispecies (WP_002892486.1, SEQ ID NO: 4).

DETAILED DESCRIPTION OF ASPECTS OF THE DISCLOSURE

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and accession numbers mentioned herein are incorporated herein by reference to disclose and describe the methods and/or materials in connection with which the publications are cited.

Terminology

As used in the context of the present disclosure, a "CadA polypeptide" refers to an *Escherichia coli* CadA polypeptide having the amino acid sequence of SEQ ID NO:2, or a biologically active variant thereof that has activity, i.e., catalyzes the decarboxylation of L-lysine to produce cadaverine. Biologically active variants include alleles, mutants, fragments, and interspecies homologs of the *E. coli* CadA polypeptide. CadA has been well characterized structurally and functionally. The protein data bank ID for the structure of CadA is 3N75. Illustrative CadA polypeptides from other species include CadA from *Klebsiella* (e.g., SEQ ID NO:3), Enterobacteriaceae (e.g., SEQ ID NO:5), and *Salmonella enterica* (e.g., SEQ ID NO:6). Additional CadA polypeptides from other species include *Serratia* sp., WP 033635725.1; and *Raoultella ornithinolytica*, YP 007874766.1. In some embodiments, a "CadA polypeptide" has at least 60% amino acid sequence identity, typically at least 65%, 70%, 75%, 80%, 85%, 90% identity; often at least 91%, 92%, 93%, 94%, 95%, 96%, 97%, 98% or 99% or greater amino acid sequence identity, over a region of at least about 200, 300, 400, 500, or more, amino acids; or over the length of the CadA polypeptide of SEQ ID NO:2. In some embodiments, a "CadA polypeptide" comprises a region that has at least 80%, at least 85%, at least 90%, at least 95%, or at least 91%, 92%, 93%, 94%, 95%, 96%, 97%, 98% or 99% or greater amino acid sequence identity over a region comprising amino acids residues that correspond to amino acids 261-509 of SEQ ID NO:2 where a native lysine present in the region, e.g., at position 320 or position 325, is substituted with another non-naturally occurring amino acid as described herein. In some embodiments, a "CadA polypeptide" has at least 60% amino acid sequence identity, often at least 65%, 70%, 75%, 80%, 85%, 90%, 91%, 92%, 93%, 94%, 95%, 96%, 97%, 98% or 99% or greater, amino acid sequence identity, preferably over a region of at least about 200, 300, 400, 500, or more, amino acids, or over the length of the CadA polypeptide of SEQ ID NO:3, SEQ ID NO:4, or SEQ ID NO:5.

A "CadA polynucleotide" as used herein refers to a polynucleotide that encodes a CadA polypeptide. A nucleic acid or polynucleotide that encodes a CadA refers to a gene, pre-mRNA, mRNA, and the like, including nucleic acids encoding variants, alleles, fragments, mutants, and interspecies homologs of the particular amino acid sequences described herein.

As used herein, the term "alkaline pH" refers to a solution or surrounding environment having a pH of greater than 7.5. In one embodiment, alkaline pH refers to a solution or surrounding environment have a pH of at least 8.0, at least 8.5, or higher.

The term "enhanced" or "improved" in the context of the production of an amino acid derivative, e.g., cadaverine, as used herein refers to an increase in the production of the amino acid derivative produced by a host cell that expresses a CadA variant polypeptide of the invention in comparison to a control counterpart cell, such as a cell of the wildtype strain or a cell of the same strain that expresses the wildtype CadA protein. In one embodiment, activity of the CadA variant is improved by at least 10%, 15% 20%, 30%, 40%, 50%, 60%, 70%, 80%, 90%, 100%, or greater, compared to CadA activity of a counterpart cell expressing a wildtype CadA, where activity is assessed by measuring the production of an amino acid derivative, typically cadaverine, produced by the host cell and control cell under identical conditions. For example, activity of a CadA variant polypeptide of the invention can be assessed by evaluating an aliquot of a culture of host cells transformed with a polynucleotide encoding the variant CadA polypeptide compared to a corresponding aliquot from a culture of counterpart host cells of the same strain that expresses wildtype CadA. By way of further illustration, the activity of a CadA variant polypeptide of the invention compared to the counterpart wildtype CadA can be determined by evaluating the production of cadaverine by cells transformed with either a vector comprising a nucleic acid sequence encoding the variant CadA polypeptide (variant host cells) or a vector comprising a nucleic acid encoding the wildtype CadA polypeptide (control host cells). Variant and control host cells that are grown under conditions to express CadA and an aliquot is incubated with lysine-HCl and PLP at a final concentration of 120 g/L and 0.1 mM, respectively at pH 8.0 for a period of time, e.g., 2 hours. Cadaverine production is measured following incubation. An exemplary assay is provided in the Examples section.

The terms "numbered with reference to", or "corresponding to," or "determined with reference to" when used in the context of the numbering of a given amino acid or polynucleotide sequence, refers to the numbering of the residues of a specified reference sequence when the given amino acid or polynucleotide sequence is compared to the reference sequence. For example, a position of a variant CadA polypeptide sequence "corresponds to" a position in SEQ ID NO:2 when the variant polypeptide is aligned with SEQ ID NO:2 in a maximal alignment.

The terms "wild type", "native", and "naturally occurring" with respect to a CadA polypeptide are used herein to refer to a CadA protein that has a sequence that occurs in nature.

In the context of this invention, the term "mutant" with respect to a mutant polypeptide or mutant polynucleotide is used interchangeably with "variant". A "non-naturally" occurring CadA variant refers to a variant or mutant CadA polypeptide that is not present in a cell in nature and that is produced by genetic modification, e.g., using genetic engineering technology or mutagenesis techniques, of a native CadA polynucleotide or polypeptide. A "variant" CadA polypeptide in the context of this disclosure includes any non-naturally occurring CadA polypeptide that comprises at least one amino acid substitution, e.g., where the at least one amino acid substitution is a substitution of a lysine residue at position 320 or 325, as determined with reference to SEQ ID NO:2. A variant CadA polypeptide of the invention may also have additional mutations relative to SEQ ID NO:2, including further substitutions, insertions, or deletions.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of this disclosure for two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An algorithm that may be used to determine whether a variant CadA polypeptide has sequence identity to SEQ ID NO:2, or another polypeptide reference sequence such as SEQ ID NO:3, SEQ ID NO:4, or SEQ ID NO:5, is the BLAST algorithm, which is described in Altschul et al., 1990, *J. Mol. Biol.* 215:403-410). Software for performing BLAST analyses is publicly available through the National Center for Biotechnology Information (on the worldwide web at ncbi.nlm.nih.gov/). Illustrative software for performing protein sequence alignments include ClustalW2 and BLASTP. For amino acid sequences, the BLASTP program uses as defaults a word size (W) of 3, an expect threshold (E) of 10, and the BLOSUM62 scoring matrix (see Henikoff & Henikoff, Proc. Natl. Acad. Sci. USA 89:10915 (1989)). In the present disclosure, polypeptide sequence identity is typically determined using BLASTP Align Sequence with the default parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Optimal alignments are typically conducted using BLASTP with default parameters.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

The term "polypeptide" as used herein includes reference to polypeptides containing naturally occurring amino acids and amino acid backbones as well as non-naturally occurring amino acids and amino acid analogs.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, Proteins (1984)). In some embodiments, conservative substitutions are employed in generating Cada variants having substitutions at sites other than a glutamate residue.

The term "promoter," as used herein, refers to a polynucleotide sequence capable of driving transcription of a nucleic acid sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different species). Similarly, a polypeptide is "heterologous" to a host cell if the native wildtype host cell does not produce the polypeptide.

The term "exogenous" refers generally to a polynucleotide sequence or polypeptide that does not naturally occur in a wild-type cell or organism, but is typically introduced into the cell by molecular biological techniques, i.e., engineering to produce a recombinant microorganism. Examples of "exogenous" polynucleotides include vectors, plasmids, and/or man-made nucleic acid constructs encoding a desired protein.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of a plasmid or vector encoding that sequence, such as to over-express or otherwise regulate the expression of the encoded protein, represents an "exogenous" copy of that gene or polynucleotide sequence. Any of the pathways, genes, or enzymes described herein may utilize or rely on an "endogenous" sequence, which may be provided as one or more "exogenous" polynucleotide sequences, or both.

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence can have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide is targeted to a position in the genome of a microorganism such that expression of the polynucleotide sequence is driven by a promoter that is present in the microorganism.

The term "host cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state. Alternatively, an "isolated peptide" or an "isolated polypeptide" and the like, as used herein, may refer to a polypeptide molecule that is free of other components of the cell, i.e., it is not associated with in vivo cellular substances.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2016).

Summary of Certain Aspects of the Disclosure

In one aspect, the invention provides a variant CadA polypeptide that comprises a mutation at lysine that resides at a position in one of sections of the protein in the core domain that are without a defined secondary structure (α, alpha helix; β, beta sheet; η, strand) (see Kanjee et al.) within those domains. These sections are the amino acids 276-299 between β10 and β11 that includes η4 and α11, the amino acids 314-326 between β11 and α12 that includes β12, the amino acids 344-357 between η6 and β14, the amino acids 454-483 between β16 and β18 that includes β17, and the amino acids 494-509 between β19 and α17, wherein the positions of the amino acids are defined with reference to SEQ ID NO:2. In some embodiments, the mutation is at a lysine residue in a region 276-509 as defined with reference to SEQ ID NO:2, where the lysine is a lysine at a position in one of the segments of the protein in the core domain that are without a defined secondary structure as explained above and where lysine is at the surface of the protein where the side chain is oriented toward the external environment.

The ability of a variant CadA of the present invention to tolerate alkaline pH also allows the use of alternative nitrogen sources that have higher pH values, such as urea and ammonia (1M solution has a pH 11.6) in fermentation reactions to generate the desired product, e.g., polyamines. These alternative nitrogen sources generate less salt waste byproduct.

CadA Polypeptide Variants

CadA is a member of the subclass of Fold Type I pyridoxal 5'-phosphate (PLP)-dependent decarboxylases. This class of proteins typically contains a N-terminal wing domain, a core domain, and a C-terminal domain. The core domain has a linker region, a PLP-binding subdomain, and subdomain 4. For CadA, the N-terminal wing domain (corresponding to residues 1 to 129 as determined with reference to SEQ ID NO:2) has a flavodoxin-like fold composed of five-stranded parallel beta-sheets sandwiched between two sets of amphipathic alpha-helices. The core domain (residues 130 to 563 as determined with reference to 563 of SEQ ID NO:2) includes: a linker region, amino acid residues 130 to 183 of SEQ ID NO:2, that form a short helical bundle; the PLP-binding subdomain, amino acids 184 to 417 of SEQ ID NO:2 that form a seven-stranded beta-sheet core surrounded by three sets of alpha-helices; and subdomain 4, amino acids 418 to 563 that form a four stranded antiparallel beta-sheet core with three alpha-helices facing outward. The C-terminal domain corresponds to amino acid residues 564 to 715 as determined with referenced to SEQ ID NO:2 that form two sets of beta sheets with an alpha-helical outer surface (Kanjee et al., *The EMBO Journal* 30, 931-944 2011).

CadA protein forms a two-fold symmetric dimer that completes the active site of each monomer. Five dimers associate to form a decamer that consist of a double-ringed structure with five-fold symmetry. The decamer associates with other decamers to form higher-order oligomers. It has been shown that in acidic conditions (pH 5), CadA predominantly exists in the oligomeric state, and less oligomers and decamers are found as the environment becomes more basic. It was estimated that 25% of the enzymes exist as dimers and 75% exist as decamers at pH 6.5, while 95% of the enzymes exist as dimers at pH 8.0 (Kanjee et al., supra). This decrease in oligomer formation coincides with the decrease in decarboxylase activity observed as the pH of the environment of the enzyme increases above 5.0.

Illustrative Cad A polypeptides from *E. coli, Salmonella enterica, Klebsiella*, and Enterobacteriaeceae are provided in SEQ ID NOS:2-5, which share greater than 90% sequence identity with one another.

CadA polypeptides of the present invention comprise at least one substitution of another amino acid for a lysine at a position in one of the segments of the protein in the core domain that are without a defined secondary structure (α, alpha helix; β, beta sheet; η, strand) (see Kanjee et al., supra); and where lysine is at the surface of the protein where the side chain is oriented toward the external environment. In the present disclosure, the amino acid that is substituted for the lysine does not occur at the corresponding position in a native CadA sequence. In some embodiments, a lysine at at least one of positions 287, 290, 319, 320, 325, 346, 357, 381, 477, or 500, as determined with reference to SEQ ID NO:2, is substituted with an amino acid that does not occur at the corresponding position in a native CadA sequence. In some embodiments, such a CadA variant polypeptides invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at least 500 or more amino acids in length, or over the length of, the CadA polypeptide of SEQ ID NO:2.

In some embodiments, a variant CadA polypeptide in accordance with the invention comprises a substitution at a lysine in the region corresponding to amino acids 314-326, between β11 and α12 that includes β12, of SEQ ID NO:2, where the lysine is at the surface of the protein and the side chain is oriented toward the external environment. In some embodiments, a variant CadA polypeptide comprises an amino acid substitution position K320 or position K325 as determined with reference to SEQ ID NO:2. In some embodiments a variant CadA polypeptide comprises more than one amino acid substitution, e.g., substitutions at both of positions 320 and 325 as determined with reference to SEQ ID NO:2. In some embodiments, the amino acid that is substituted for a lysine is selected from the group of amino acids consisting of alanine, arginine, asparagine, aspartic acid, cysteine, glutamine, glutamic acid, glycine, histidine, isoleucine, leucine, methionine, phenylalanine, proline, serine, threonine, tryptophan, tyrosine, or valine, where the mutant does not have the same amino acid as the wild-type sequence (SEQ ID NO: 2, 3, 4, or 5) at the same position. In some embodiments, the amino acid that is substituted for a lysine is methionine. The sulfur of methionine can act as either a nucleophile or an electrophile and does not need a proton to interact with other amino acid groups. A methionine may thus further stabilize a protein-protein interaction at that site. In some embodiments, the amino acid that is substituted for a lysine, e.g., at a position corresponding to K320 or K325, is selected from the group consisting of C, H, E, S, A, F, L, M, N, R, V, Y, D, G, I, P, Q, T, and W. In some embodiments, the amino acid that is substituted for a lysine is selected from the group consisting A, C, E, G, H, I, L, M, S, V, and Y. In some embodiments, the amino acid that is substituted for a lysine is selected from the group consisting of C, E, G, L, V, and Y.

In some embodiments, the variant CadA polypeptide is a variant of CadA from *E. coli* in which at least one or both of the lysine residues at positions K320 and K325 is substituted with another amino acid.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:2; and has a substitution at a lysine residue at at least one of positions K320 or K325 as determined with reference to SEQ ID NO:2. In some embodiments, the substitution is at position K320. In some embodiments, the amino acid substituted for K320 is A, C, E, H, G, I, L, M, S, V, or Y. In other embodiments, the amino acid substituted for lysine is C, E, G, L, V, or Y.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:3; and has a substitution at a lysine residue at at least one of positions K320 or K325 as determined with reference to SEQ ID NO:3. In some embodiments, the substitution is at position K320. In some embodiments, the amino acid substituted for K320 is A, C, E, H, G, I, L, M, S, V, or Y. In other embodiments, the amino acid substituted for the lysine is C, E, G, L, V, or Y.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:4; and has a substitution at a lysine residue at at least one of positions K320 or K325 as determined with reference to SEQ ID NO:4. In some embodiments, the substitution is at position K320. In some embodiments, the amino acid substituted for K320 is A, C, E, H, G, I, L, M, S, V, or Y. In other embodiments, the amino acid substituted for the lysine is C, E, G, L, V, or Y.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:5; and has a substitution at a lysine residue at at least one of positions K320 or K325 as determined with reference to SEQ ID NO:5. In some embodiments, the amino acid substituted for K320 is A, C, E, H, G, I, L, M, S, V, or Y. In other embodiments, the amino acid substituted for the lysine is C, E, G, L, V, or Y.

In some embodiments, any one of the CadA polypeptide variants having a substitution at a lysine residue as described herein further comprises at least one substitution at a glutamic acid at position E291, E344, E355, E463, E482, and E499 as determined with reference to SEQ ID NO:2. In some embodiments the CadA variant polypeptide having a substitution at a lysine residue as described herein comprises more than one amino acid substitution, e.g., 2, 3, or more substitutions, at positions E291, E344, E355, E463, E482, and E499 as determined with reference to SEQ ID NO:2. In some embodiments, any one of the CadA polypeptide variants having a substitution at a lysine residue as described herein further comprises at least one substitution at a glutamic acid (also referred to herein as glutamate) at positions E291 or E355 as determined with reference to SEQ ID NO:2. In some embodiments, the amino acid that is substituted for the glutamic acid is selected from the group of amino acids consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, where the mutant does not have the same amino acid as the wild-type sequence (SEQ ID NO: 2, 3, 4, or 5) at the same position. In some embodiments, the amino acid that is substituted for a glutamate has the ability to donate a hydrogen for hydrogen bond formation. For example, C, Y, K, and N have pKa valuates greater than 7, so their protonation state does not change when the pH increases from 5 to 8. Therefore, any hydrogen bond formed at these positions is more stable compared to when glutamate, which has an acidic pKa, is present at those positions. The sulfur of M can act as either a nucleophile or an electrophile and does not need a proton to interact with other amino acid groups. M may thus further stabilize a protein-protein interaction at that site. In some embodiments, the amino acid that is substituted for a glutamate is selected from the group consisting of C, H, K, S, A, F, L, M, N, R, V, Y, D, G, I, P, Q, T, and W. In some embodiments, the amino acid that is substituted for a glutamate is selected from the group consisting of C, H, K, S, A, F, L, M, N, R, V, and Y. In some embodiments, the amino acid that is substituted for a glutamate is selected from the group consisting of C, Y, K, S, H, R, M, and N. In some embodiments, the amino acid that is substituted for a glutamate is selected from the group consisting of C, H, K, and S.

In some embodiments, a variant CadA polypeptide of the invention has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of at 500 or more amino acids in length, or over the length of, the CadA polypeptide of SEQ ID NO:2; has a substitution at a lysine residue at at least one of positions K320 or K325 as determined with reference to SEQ ID NO:2; and further comprises a substitutions at position E291, E344, E355, E463, E482, and E499, e.g., as described in the preceding paragraph. In some embodiments, the substitution is at E291 or E355. In some embodiments, the CadA variant comprises a substitution at K320 and E355. In some embodiments, the CadA variant comprises a C substituted for lysine at position 320 and a C substituted for glutamic acid at position 355 as determined with reference to SEQ ID NO:2.

Nucleic Acids Encoding CadA Variant Polypeptides

Isolation or generation of CadA polynucleotide sequences can be accomplished by a number of techniques. In some embodiments, oligonucleotide probes and based on the sequences disclosed here can be used to identify the desired polynucleotide in a cDNA or genomic DNA library from a desired bacteria species. Desired substitutions may be introduced into the CadA-encoding polynucleotide sequence using appropriate primers, e.g., as illustrated in the Examples section, to incorporate the desired changes into the polynucleotide sequence. For instance, PCR may be used to amplify the sequences of the genes directly from mRNA, from cDNA, from genomic libraries or cDNA libraries and to introduce desired substitutions.

Appropriate primers and probes for identifying a CadA polynucleotide in bacteria can be generated from comparisons of the sequences provided herein or generated based on a CadA polynucleotide sequence from another bacteria. For a general overview of PCR see PCR Protocols: A Guide to Methods and Applications. (Innis, M, Gelfand, D., Sninsky, J. and White, T., eds.), Academic Press, San Diego (1990). Illustrative primer sequences are shown in the Table of Primers in the Examples section.

Nucleic acid sequences encoding an acid decarboxylase polypeptide for use in the disclosure includes genes and gene products identified and characterized by techniques such as hybridization and/or sequence analysis using illustrative nucleic acid sequences, e.g., a cadA polynucleotide sequence of SEQ ID NO:1. In some embodiments, a host cell is genetically modified by introducing a nucleic acid sequence having at least 60% identity, or at least 70%, 75%, 80%, 85%, or 90% identity, or 95% identity, or greater, to an acid decarboxylase polynucleotide, e.g., a cadA polynucleotide of SEQ ID NO:1, wherein the nucleic acid comprises a codon that encodes the desired amino acid to be substituted.

Nucleic acid sequences encoding a CadA variant protein in accordance with the invention that confers increased production of an amino acid derivative, e.g., cadaverine, to a host cell, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See e.g., Henaut and Danchin in "*Escherichia coli* and *Salmonella*," Neidhardt, et al. Eds., ASM Pres, Washington D.C. (1996), pp. 2047-2066; *Nucleic Acids Res.* 20:2111-2118; Nakamura et al., 2000, *Nucl. Acids Res.* 28:292).

Preparation of Recombinant Vectors

Recombinant vectors for expression of a variant CadA protein can be prepared using methods well known in the art. For example, a DNA sequence encoding a CadA variant polypeptide, can be combined with transcriptional and other regulatory sequences which will direct the transcription of the sequence from the gene in the intended cells, e.g., bacterial cells such as H. *alvei*, E. *coli*, or C. *glutamicum*. In some embodiments, an expression vector that comprises an expression cassette that comprises the gene encoding the CadA variant polypeptide further comprises a promoter operably linked to the nucleic acid sequence encoding the CadA variant polypeptide. In other embodiments, a promoter and/or other regulatory elements that direct transcription of the cadA polynucleotide encoding a variant CadA polypeptide are endogenous to the host cell and an expression cassette comprising the cadA gene is introduced, e.g., by homologous recombination, such that the exogenous gene is operably linked to an endogenous promoter and is expression driven by the endogenous promoter.

As noted above, expression of the polynucleotide encoding a CadA variant polypeptide can be controlled by a number of regulatory sequences including promoters, which may be either constitutive or inducible; and, optionally, repressor sequences, if desired. Examples of suitable promoters, especially in a bacterial host cell, are the promoters obtained from the *E. coli* lac operon and other promoters derived from genes involved in the metabolism of other sugars, e.g., galactose and maltose. Additional examples include promoters such as the trp promoter, bla promoter bacteriophage lambda PL, and T5. In addition, synthetic promoters, such as the tac promoter (U.S. Pat. No. 4,551, 433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra. Additional promoters include promoters described by Jensen & Hammer, *Appl. Environ. Microbiol.* 64:82, 1998; Shimada, et al., *J. Bacteriol.* 186: 7112, 2004; and Miksch et al., *Appl. Microbiol. Biotechnol.* 69:312, 2005.

In some embodiments, a promoter that influences expression of a cadA gene encoding a CadA variant polypeptide of the invention may be modified to increase expression. For example, an endogenous CadA promoter may be replaced by a promoter that provides for increased expression compared to the native promoter.

An expression vector may also comprise additional sequences that influence expression of a polynucleotide encoding the CadA variant polypeptide. Such sequences include enhancer sequences, a ribosome binding site, or other sequences such as transcription termination sequences, and the like.

A vector expressing a polynucleotide encoding a CadA variant polypeptide of the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s)

into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as *E. coli, H. alvei*, or *C. glutamicum*.

Although any suitable expression vector may be used to incorporate the desired sequences, readily available bacterial expression vectors include, without limitation: plasmids such as pSClO1, pBR322, pBBR1MCS-3, pUR, pET, pEX, pMRlOO, pCR4, pBAD24, p15a, pACYC, pUC, e.g., pUC18 or pUC19, or plasmids derived from these plasmids; and bacteriophages, such as M13 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified host cell that is engineered to express a CadA variant polypeptide of the invention. A genetically modified host strain of the present invention typically comprises at least one additional genetic modification to enhance production of an amino acid or amino acid derivative relative to a control strain that does not have the one additional genetic modification, e.g., a wildtype strain or a cell of the same strain without the one additional genetic modification. An "additional genetic modification to enhance production of an amino acid or amino acid derivative" can be any genetic modification. In some embodiments, the genetic modification is the introduction of a polynucleotide that expresses an enzyme involved in the synthesis of the amino acid or amino acid derivative. In some embodiments, the host cell comprises multiple modifications to increase production, relative to a wildtype host cell, of an amino acid or amino acid derivative.

In some aspects, genetic modification of a host cell to express a CadA variant polypeptide is performed in conjunction with modifying the host cell to overexpress one or more lysine biosynthesis polypeptides.

In some embodiments, a host cell may be genetically modified to express one or more polypeptides that affect lysine biosynthesis. Examples of lysine biosynthesis polypeptides include the *E. coli* genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PO, ThrA, AceA, AceB, GltB, AceE, SdhA, MurE, SpeE, SpeG, PuuA, PuuP, and YgjG, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes involved in cadaverine production. Illustrative genes encoding lysine biosynthesis polypeptides are provided below.

| Protein | Gene | EC Number | GenBank Accession No. |
|---|---|---|---|
| α-ketogultarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde dehydrogenase (Asd) | asd | 1.2.1.11 | AAC76458.1 |
| dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.1 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gitA | 2.3.3.1/2.3.3.16 | AAC73814.1 |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |

-continued

| Protein | Gene | EC Number | GenBank Accession No. |
|---|---|---|---|
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate: meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |
| putrescine importer (PuuP) | puuP | NA | AAC74378.2 |
| putrescine/cadaverine aminotransferase (YgjQ) | ygjG | 2.6.1.82 | AAC76108.3 |

In some embodiments, a host cell may be genetically modified to attenuate or reduce the expression of one or more polypeptides that affect lysine biosynthesis. Examples of such polypeptides include the *E. coli* genes Pck, Pgi, DeaD, CitE, MenE, PoxB, AceA, AceB, AceE, RpoC, and ThrA, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes attenuated to increase cadaverine production. Illustrative genes encoding polypeptides whose attenuation increases lysine biosynthesis are provided below.

| Protein | Gene | EC Number | GenBank Accession No. |
|---|---|---|---|
| PEP carboxykinase (Pck) | pck | 4.1.1.49 | NP_417862 |
| Glucose-6-phosphate isomerase (Pgi) | pgi | 5.3.1.9 | NP_418449 |
| DEAD-box RNA helicase (DeaD) | deaD | | NP_417631 |
| citrate lyase (CitE) | citE | 4.1.3.6/4.1.3.34 | NP_415149 |
| o-succinylbenzoate-CoA ligase (MenE) | menE | 6.2.1.26 | NP_416763 |
| pyruvate oxidase (PoxB) | poxB | 1.2.2.2 | NP_415392 |
| isocitrate lyase (AceA) | aceA | 4.1.3.1 | NP_418439 |
| malate synthase A (AceB) | aceB | 2.3.3.9 | NP_418438 |
| pyruvate dehydrogenase (aceE) | aceE | 1.2.4.1 | NP_414656 |
| RNA polymerase b' subunit (RpoC) | rpoC | 2.7.7.6 | NP_418415 |
| aspartokinase I (ThrA) | thrA | 2.7.2.4/1.1.1.3 | NP_414543 |

Nucleic acids encoding a lysine biosynthesis polypeptide may be introduced into the host cell along with a polynucleotide encoding a CadA variant polypeptide, e.g., encoded on a single expression vector, or introduced in multiple expression vectors at the same time. Alternatively, the host cell may be genetically modified to overexpress one or more lysine biosynthesis polypeptides before or after the host cells genetically modified to express a CadA variant polypeptide.

A host cell engineered to express a CadA variant polypeptide is typically a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus *Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella,* or *Klebsiella* taxonomical classes. In some embodiments, the host cells are members of the genus *Escherichia, Hafnia,* or *Corynebacterium*. In some embodiments, the host cell is an *Escherichia coli, Hafnia alvei,* or *Corynebacterium glutamicum* host cell. In some embodiments, the host cell is *Escherichia coli*. In some embodiments, the host cell is Hafnia *alvei*. In some embodiments, the host cell is *Corynebacterium glutamicum*.

In some embodiments, the host cell is a gram-positive bacterial host cell, such as a *Bacillus* sp., e.g., *Bacillus subtilis* or *Bacillus lichemformis*; or another *Bacillus* sp. such as *B. alcalophilus, B. aminovorans, B. amyloliquefaciens, B. caldolyticus, B. circulans, B. stearothermophilus, B. thermoglucosidasius, B. thuringiensis* or *B. vulgatis*.

Host cells modified in accordance with the invention can be screened for increased production of lysine or a lysine derivative, such as cadaverine, as described herein.

In some embodiments, a CadA variant polypeptide of the present invention may be recovered from a host cell that expresses the variant polypeptide. In some embodiments, the recovered variant protein may be immobilized onto a solid substrate or inert material to form an immobilized enzyme. In one embodiment, the immobilized enzyme may have improved operational stability than the soluble form of the fusion protein.

Methods of Producing Lysine or a Lysine Derivative.

A host cell genetically modified to overexpress a CadA variant polypeptide of the invention can be employed to produce lysine or a derivative of lysine. In some embodiments, the host cell produces cadaverine. Thus, for example, to produce cadaverine, a host cell genetically modified to express a CadA variant polypeptide as described herein can be cultured under conditions suitable to allow expression of the polypeptide and expression of genes that encode the enzymes that are used to produce lysine and/or cadaverine. A host cell modified in accordance with the invention to express a CadA variant polypeptide provides a higher yield of cadaverine relative to a counterpart host cell that expresses native CadA.

Host cells may be cultured using well known techniques (see, e.g., the illustrative conditions provided in the examples section.

In some embodiments, host cells are cultured using nitrogen sources that are not salts (e.g., ammonium sulfate or ammonium chloride), such as ammonia or urea. Host cells may be cultured at an alkaline pH during cell growth or enzyme production.

The lysine or lysine derivative then be separated and purified using known techniques. Lysine or lysine derivatives, e.g., cadaverine, produced in accordance with the invention may then be used in any known process, e.g., to produce a polyamide.

In some embodiments, lysine may be converted to caprolactam using chemical catalysts or by using enzymes and chemical catalysts.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

We hypothesized that the decamer-decamer interface contains segments of the protein in the core domain, and is composed of sections of the protein without a defined secondary structure ($\alpha$, alpha helix; $\beta$, beta sheet; $\eta$, strand) (see Kanjee et al.) within those domains. These sections are the amino acids 276-299 between $\beta$10 and $\beta$11 that includes $\eta$4 and $\alpha$11, the amino acids 314-326 between $\beta$11 and $\alpha$12 that includes $\beta$12, the amino acids 344-357 between $\eta$6 and $\beta$14, the amino acids 454-483 between $\beta$16 and $\beta$18 that includes $\beta$17, and the amino acids 494-509 between $\beta$19 and $\alpha$17. These examples show that lysine residues at these positions can be substituted to increase production of cadaverine by host cells that are genetically modified to express the CadA variant polypeptide.

Example 1: Construction of Plasmid Vectors that Encode CadA

A plasmid vector containing wild-type *E. coli* cadA (SEQ ID NO: 1), which encodes the lysine decarboxylase CadA (SEQ ID NO: 2), was amplified from the *E. coli* MG1655 K12 genomic DNA using the PCR primers cadA-F and cadA-R (FIG. 1), digested using the restriction enzymes SacI and XbaI, and ligated into pUC18 to generate the plasmid pCIB60. The 5' sequence upstream of the cadA gene was optimized using the PCR primers cadA-F2 and cadA-R2 to create pCIB71.

Example 2: Construction of Plasmid Vectors that Encode CadA with Cysteine Mutations at the Predicted Interfacial Amino Acid Residues Primer pairs were designed to introduce mutations into the cadA gene of pCIB71 to modify the amino acid at position 287, 290, 319, 320, 325, 346, 357, 381, 477, or 500 of CadA to cysteine using Quickchange PCR. The mutations were verified using DNA sequencing, and the plasmids carrying the cysteine mutations were labeled pCIB71-K287C, pCIB71-K290C, pCIB71-K319C, pCIB71-K320C, pCIB71-K325C, pCIB71-K346C, pCIB71-K357C, pCIB71-K381C, pCIB71-K477C, or pCIB71-K500C.

Example 3: Lysine Decarboxylase Activity of Mutant CadA Polypeptides with Cysteine Mutations at the Predicted Interfacial Amino Acid Residues

*H. alvei* was transformed with pCIB71-K287C, pCIB71-K290C, pCIB71-K319C, pCIB71-K320C, pCIB71-K325C, pCIB71-K346C, pCIB71-K357C, pCIB71-K381C, pCIB71-K477C, or pCIB71-K500C. Three single colonies from each transformation were grown overnight at 37° C. in 4 mL of LB medium with ampicillin (100 µg/mL). The following day, 0.7 mL of each overnight culture was added to 0.3 mL of lysine-HCl and PLP to a final concentration of 120 g/L and 0.1 mM, respectively. The final mixture was adjusted to pH 8.0 with 1M NaOH. Each mixture was incubated at 37° C. for 2 hours. Cadaverine production from each sample was quantified using NMR, and yield was calculated by dividing the molar amount of cadaverine produced by the molar amount of lysine added. The average yield from each sample relative to the average yield from H. alvei transformed with pCIB71 after 2 hours is presented in Table 1.

TABLE 1

Relative cadaverine yield at pH 8 by H. alvei strains expressing plasmids encoding CadA polypeptides with mutations at the predicted interfacial amino acid residues.

| Plasmid | Relative Yield (%) |
| --- | --- |
| pCIB71 | 100 |
| pCIB71-K287C | 84 |
| pCIB71-K290C | 93 |
| pCIB71-K319C | 74 |
| pCIB71-K320C | 187 |
| pCIB71-K325C | 106 |
| pCIB71-K346C | 89 |
| pCIB71-K357C | 87 |
| pCIB71-K381C | 100 |
| pCIB71-K477C | 77 |
| pCIB71-K500C | 87 |

As shown in Table 1, two mutations improved the activity of the CadA polypeptide at pH 8.0. The mutation K320C significantly increased relative yield by more than 30%. The mutation K325C increased yield by 6%.

Example 4: Construction of Plasmid Vectors that Encode CadA with a Mutation at K320

Primer pairs were designed to introduce the desired mutations to modify the amino acid at position 320 of the cadA gene in pCIB71 using Quickchange PCR. The mutations were verified using DNA sequencing, and the plasmids carrying each mutation at amino acid position 320 were labeled pCIB71-K320X, where X is the amino acid that replaced the lysine residue.

Example 5: Lysine Decarboxylase Activity of Mutant CadA Polypeptides with a K320X Mutation

*H. alvei* was transformed with pCIB71-K320X. Three single colonies from each transformation were grown overnight at 37° C. in 4 mL of LB medium with ampicillin (100 µg/mL). The following day, 0.7 mL of each overnight culture was added to 0.3 mL of lysine-HCl and PLP to a final concentration of 120 g/L and 0.1 mM, respectively. The final mixture was adjusted to pH 8.0 with 1M NaOH. Each mixture was incubated at 37° C. for 2 hours. Cadaverine production from each sample was quantified using NMR, and yield was calculated by dividing the molar amount of cadaverine produced by the molar amount of lysine added. The yield from each sample relative to the average yield from *H. alvei* transformed with pCIB71 after 2 hours is presented in Table 2.

TABLE 2

Relative cadaverine yield at pH 8 by H. alvei strains expressing plasmids encoding CadA polypeptides with mutations at amino acid position 320.

| Plasmid | Relative Yield (%) |
| --- | --- |
| pCIB71 | 100 |
| pCIB71-K320A | 117 |
| pCIB71-K320C | 191 |
| pCIB71-K320D | 98 |
| pCIB71- K320E | 126 |
| pCIB71-K320F | 100 |
| pCIB71-K320G | 140 |
| pCIB71-K320H | 115 |
| pCIB71-K320I | 117 |
| pCIB71-K320L | 148 |
| pCIB71-K320M | 113 |
| pCIB71-K320N | 87 |
| pCIB71-K320P | 57 |
| pCIB71-K320Q | 68 |
| pCIB71-K320R | 94 |
| pCIB71-K320S | 111 |
| pCIB71-K320T | 96 |
| pCIB71-K320V | 126 |
| pCIB71-K320W | 87 |
| pCIB71-K320Y | 129 |

As shown in Table 2, several mutations at amino acid position 291 improved the activity of the CadA polypeptide at pH 8.0. The mutations K320C, K320E, K320G, K320L, K320V, and K320Y increased relative yield by more than 25%. The mutations K320A, K320H, K320I, K320M, and K320S also increased yield. The mutations K320D, K320F, K320R, and K320T had little effect on yield. The remaining mutations K320N, K320P, K320Q, and K320W decreased yield.

Example 6: In Vitro Kinetic Analysis of Mutant CadA Polypeptides at Alkaline pH Conditions 100 mL samples of *H. avlei* transformed with either pCIB71, pCIB71-K320C, pCIB71-K320G, and pCIB71-K320L were lysed with a french press. The lysed samples were centrifuged, and the supernatant was separated from the pellet in order to perform in vitro experiments. Each reaction was performed in Tris-HCl buffer (50 mM Tris-HCl either pH 6 or 8, 25 mM NaCl, 2 mM EDTA) with 120 g/L lysine-HCl and 0.1 mM PLP. The reaction rate of each lysed sample was measured using NMR by sampling the amount of lysine converted in the presence of PLP into cadaverine every 1.6 minutes for a total of 20 minutes, and taking the slope of the linear portion of the yield curve. The samples were diluted so that the reaction rate U (mmol/min/mL) of each sample was 4. The kinetic constants Vmax and Km for lysine of each lysed samples was measured using the same U at an initial pH of either 6 or 8. The results of the kinetic analysis of the two samples are shown in Table 3.

TABLE 3

Kinetic analysis of normalized Vmax of lysed samples of H. avlei expressing plasmids encoding wild-type or mutant CadA polypeptides under different pH conditions.

| pH | pCIB71 | pCIB71-K320C | pCIB71-K320G | pCIB71-K320L |
| --- | --- | --- | --- | --- |
| 6 | 100% | 100% | 100% | 100% |
| 8 | 76% | 94% | 96% | 94% |

As shown in Table 3, wild-type CadA (pCIB71) lost 24% of activity at pH 8 compared to pH 6. Surprisingly, the mutant CadA polypeptides (pCIB71-K320C, pCIB71-K320G, and pCIB71-K320L) showed significantly higher activity at pH 8 compared to wild-type CadA polypeptide despite there being no significant difference in activity between the wild-type and mutants at pH 6.

Example 7: Construction of Plasmid Vectors that Encode CadA with Mutations at Position 320 and Either Position 291 or 355

Primer pairs were designed to modify the cadA gene in plasmids pCIB71-E291C and pCIB71-E355C to introduce a mutation at amino acid 320 of the CadA polypeptide. Plasmids pCIB71-E291C and pCIB81-E255C were generated using methodology as explained in Example 2 and contain cadA gene constructs encoding the mutations E291C and E355C, respectively. Quickchange PCR using methodology as indicated in Examples 2 and 4 was employed to introduce the desired mutation at position 320. The mutations were verified using DNA sequencing, and the plasmids carrying each mutation at amino acid position 320 were labeled pCIB71-E291C-K320X and pCIB71-E355C-K320X, where X is the amino acid that replaced the lysine residue.

Example 8: Lysine Decarboxylase Activity of CadA Polypeptides with Mutations at 320 and Either E291C or E355C

*H. alvei* was transformed with pCIB71, pCIB71-E291C-K320X and pCIB71-E355C-K320X. Three single colonies from each transformation were grown overnight at 37° C. in 4 mL of LB medium with ampicillin (100 µg/mL). The following day, 0.7 mL of each overnight culture was added to 0.3 mL of lysine-HCl and PLP to a final concentration of 120 g/L and 0.1 mM, respectively. The final mixture was adjusted to pH 8.0 with 1M NaOH. Each mixture was incubated at 37° C. for 2 hours. Cadaverine production from each sample was quantified using NMR, and yield was calculated by dividing the molar amount of cadaverine produced by the molar amount of lysine added. The yield from each sample relative to the average yield from *H. alvei* transformed with pCIB71 after 2 hours is presented in Table 4.

TABLE 4

Relative cadaverine yield at pH 8 by H. alvei strains expressing plasmids encoding CadA polypeptides with mutations at amino acid position 468.

| Plasmid | Relative Yield (%) |
| --- | --- |
| pCIB71 | 100 |
| pCIB71-E291C-K320C | 78 |

TABLE 4-continued

Relative cadaverine yield at pH 8 by H. alvei strains expressing plasmids encoding CadA polypeptides with mutations at amino acid position 468.

| Plasmid | Relative Yield (%) |
| --- | --- |
| pCIB71- E291C-K320G | 113 |
| pCIB71- E291C-K320L | 115 |
| pCIB71-E355C-K320C | 220 |
| pCIB71- E355C-K320G | 131 |
| pCIB71- E355C-K320L | 146 |

As shown in Table 4, the majority of mutant CadA polypeptides with two mutations increased yield at pH 8 relative to the wild-type CadA polypeptide, with the exception of the E291C-K320C mutant. Surprisingly, the double mutant E355C-K320C showed more than 2X the yield compared to the wild-type polypeptide at pH 8.

Example 9: Effect of Enzyme Concentration on Retention of Lysine Decarboxylase Activity According to the literature, the activity of CadA at pH 8 is significantly less than its activity at pH 6 due to a structural change from a high oligomer state to a low oligomer state. The activity of the wild-type and mutant CadA polypeptides was compared at pH 6 and pH 8, in order to determine whether the mutations can increase the activity of the CadA polypeptide under alkaline pH conditions.

Samples of 100 mL of H. avlei transformed with either pCIB71 and pCIB71-K320C were lysed with a french press. The lysed samples were centrifuged, and the supernatant was separated from the pellet in order to perform in vitro experiments. Each reaction was performed in Tris-HCl buffer (50 mM Tris-HCl either pH 6 or 8, 25 mM NaCl, 2 mM EDTA) with 120 g/L lysine-HCl and 0.1 mM PLP. The reaction rate of each lysed sample was measured using NMR by sampling the amount of lysine converted in the presence of PLP into cadaverine every 1.6 minutes for a total of 20 minutes, and taking the slope of the linear portion of the yield curve. The samples were diluted so that the reaction rate per volume (mmol/min/mL, U) of lysed sample was the same. The kinetic constant Vmax of each lysed samples was measured using the same U at an initial pH of either 6 or pH 8. By normalizing for U, the concentration of active enzyme in each sample is the same. The results of the kinetic analysis of the two samples are

TABLE 5

Percent change in Vmax from pH 6 to 8 of lysed samples of H. avlei expressing plasmids encoding either wild-type CadA or mutant polypeptides at different concentrations of enzyme lysate as measured by U.

| U | pCIB71 | pCIB71-K320C |
| --- | --- | --- |
| 0.5 | −48% | −26% |
| 1 | −37% | −27% |
| 2 | −30% | −23% |
| 4 | −26% | −15% |
| 8 | −27% | −17% |

Based on the data in Table 5, the loss of activity from pH 6 to pH 8 is concentration dependent. At lower concentrations of either the wild-type (pCIB71) or mutant (pCIB71-K320C) CadA polypeptide, the enzyme is more sensitive to alkaline pH compared to higher concentrations of the polypeptide. This is indicated by the loss of 48% of activity for 0.5 U compared to a loss of only 27% for 8 U when going from pH 6 to pH 8 for the wild-type polypeptide. However, the mutant CadA polypeptide shows a reduced loss of activity compared to the wild-type polypeptide at all enzyme concentrations. The mutant polypeptide lost only 26% activity at 0.5 U and only 17% activity at 8 U when going from pH 6 to pH 8.

Example 10. Activity of Immobilized CadA Lysine Decarboxylases

CadA polypeptide immobilized onto epoxy resin was prepared by first harvesting an enzyme solution from a fermentation broth, diluting the enzyme solution using a 0.2 M citric acid buffer to a concentration of 500 U/g, and bringing the diluted solution to a pH of 7.5-8.0. Epoxy resin was then added to the dilute enzyme solution, and mixed well while incubating at 20° C. for 3 days. The immobilized enzyme mixture was washed with water before use.

An amount of immobilized wild-type CadA and mutant CadA K320C equivalent of 10,000 U of activity were assayed over the course of multiple days in order to test their stability during the conversion of lysine to cadaverine. The wild-type and mutant immobilized enzymes were packed into separate glass columns. A 400 g solution containing 10,000 U of immobilized enzyme, 120 g/L lysine-HCl, and 0.1 mM PLP was circulated for 3 hours. The cadaverine yield of the solution was measured using NMR. The columns were then washed with water and a new solution containing lysine and PLP was circulated through the columns. This procedure was repeated a total of 23 times. The cadaverine yield from each round of lysine conversion for the columns containing either immobilized wild-type or mutant CadA is shown in Table 6.

TABLE 6

Cadaverine yield of immobilized wild-type and mutant CadA polypeptides.

| Round | pCIB71 | pCIB71-K320C |
| --- | --- | --- |
| 1 | 99% | 99% |
| 2 | 98% | 99% |
| 3 | 97% | 99% |
| 4 | 90% | 98% |
| 5 | 92% | 98% |
| 6 | 90% | 98% |
| 7 | 90% | 98% |
| 8 | 89% | 98% |
| 9 | 87% | 98% |
| 10 | 86% | 98% |
| 11 | 86% | 98% |
| 12 | 86% | 98% |
| 13 | 85% | 98% |
| 14 | 84% | 98% |
| 15 | 84% | 97% |
| 16 | 83% | 97% |
| 17 | 83% | 97% |
| 18 | 82% | 97% |
| 19 | 81% | 97% |
| 20 | 80% | 97% |
| 21 | 79% | 97% |
| 22 | 78% | 97% |
| 23 | 76% | 96% |
| 24 | 76% | 96% |

As shown in Table 6, the immobilized mutant CadA (pCIB71-K320C) polypeptide was able to maintain a cadaverine yield of 96% to 99% across 24 rounds of lysine conversion reactions. However, the immobilized wild-type CadA polypeptide (pCIB71) was only able to maintain a cadaverine yield of 76% to 99% across 24 rounds. After the 23rd reuse, the yield of the column with the immobilized wild-type CadA had decreased by 23% (99%-76%), while that for the immobilized mutant CadA had only decreased by 3% (99%-96%). The average yield across 24 rounds for the column with the immobilized wild-type CadA was 86%, while that with the immobilized mutant CadA was 98%.

TABLE 7

Table of plasmids and strains for lysine mutations used in Examples.

| Host | Protein(s) Overexpressed | Plasmid |
|---|---|---|
| Hafnia alvei | CadA | pCIB71 |
| Hafnia alvei | CadA K320A | pCIB71-K320A |
| Hafnia alvei | CadA K320C | pCIB71-K320C |
| Hafnia alvei | CadA K320D | pCIB71-K320D |
| Hafnia alvei | CadA K320E | pCIB71-K320E |
| Hafnia alvei | CadA K320F | pCIB71-K320F |
| Hafnia alvei | CadA K320G | pCIB71-K320G |
| Hafnia alvei | CadA K320H | pCIB71-K320H |
| Hafnia alvei | CadA K320I | pCIB71-K320I |
| Hafnia alvei | CadA K320L | pCIB71-K320L |
| Hafnia alvei | CadA K320M | pCIB71-K320M |
| Hafnia alvei | CadA K320N | pCIB71-K320N |
| Hafnia alvei | CadA K320P | pCIB71-K320P |
| Hafnia alvei | CadA K320Q | pCIB71-K320Q |
| Hafnia alvei | CadA K320R | pCIB71-K320R |
| Hafnia alvei | CadA K320S | pCIB71-K320S |
| Hafnia alvei | CadA K320T | pCIB71-K320T |
| Hafnia alvei | CadA K320V | pCIB71-K320V |
| Hafnia alvei | CadA K320W | pCIB71-K320W |
| Hafnia alvei | CadA K320Y | pCIB71-K320Y |
| Hafnia alvei | CadA E291C, K320C | pCIB71-E291C-K320C |
| Hafnia alvei | CadA E291C, K320G | pCIB71-E291C-K320G |
| Hafnia alvei | CadA E291C, K320L | pCIB71-E291C-K320L |
| Hafnia alvei | CadA E355C, K320C | pCIB71-E355C-K320C |
| Hafnia alvei | CadA E355C, K320G | pCIB71-E355C-K320G |
| Hafnia alvei | CadA E355C, K320L | pCIB71-E355C-K320L |

TABLE 8

Table of primer sequences (lysine mutations) used in Examples.

| Name | Sequence (5'-3') |
|---|---|
| cadA-F | GGCGAGCTCACACAGGAAACAGACCATGAACGTTATTGCAATATTGAATCAC |
| cadA-R | GGCTCTAGACCACTTCCCTTGTACGAGC |
| cadA-F2 | ATTTCACACAGGAAACAGCTATGAACGTTATTGCAATATTGAAT |
| cadA-R2 | AGCTGTTTCCTGTGTGAAAT |
| K320A-F | ACCGACTTCATCAAGGCAACACTGGATGTGAAATCCATC |
| K320A-R | GATTTCACATCCAGTGTTGCCTTGATGAAGTCGGTGTTG |
| K320C-F | ACCGACTTCATCAAGTGCACACTGGATGTGAAATCCATC |
| K320C-R | GATTTCACATCCAGTGTGCACTTGATGAAGTCGGTGTTG |
| K320D-F | ACCGACTTCATCAAGGACACACTGGATGTGAAATCCATC |
| K320D-R | GATTTCACATCCAGTGTGTCCTTGATGAAGTCGGTGTTG |
| K320E-F | ACCGACTTCATCAAGGAAACACTGGATGTGAAATCCATC |
| K320E-R | GATTTCACATCCAGTGTTTCCTTGATGAAGTCGGTGTTG |
| K320E-F | ACCGACTTCATCAAGTTCACACTGGATGTGAAATCCATC |
| K320E-R | GATTTCACATCCAGTGTGAACTTGATGAAGTCGGTGTTG |
| K320G-F | ACCGACTTCATCAAGGGAACACTGGATGTGAAATCCATC |
| K320G-R | GATTTCACATCCAGTGTTCCCTTGATGAAGTCGGTGTTG |
| K320H-F | ACCGACTTCATCAAGCATACACTGGATGTGAAATCCATC |
| K320H-R | GATTTCACATCCAGTGTATGCTTGATGAAGTCGGTGTTG |
| K320I-F | ACCGACTTCATCAAGATCACACTGGATGTGAAATCCATC |
| K320I-R | GATTTCACATCCAGTGTGATCTTGATGAAGTCGGTGTTG |
| K320L-F | ACCGACTTCATCAAGCTGACACTGGATGTGAAATCCATC |
| K320L-R | GATTTCACATCCAGTGTCAGCTTGATGAAGTCGGTGTTG |
| K320M-F | ACCGACTTCATCAAGATGACACTGGATGTGAAATCCATC |
| K320M-R | GATTTCACATCCAGTGTCATCTTGATGAAGTCGGTGTTG |
| K320N-F | ACCGACTTCATCAAGAACACACTGGATGTGAAATCCATC |
| K320N-R | GATTTCACATCCAGTGTGTTCTTGATGAAGTCGGTGTTG |
| K320P-F | ACCGACTTCATCAAGCCAACACTGGATGTGAAATCCATC |
| K320P-R | GATTTCACATCCAGTGTTGGCTTGATGAAGTCGGTGTTG |
| K320Q-F | ACCGACTTCATCAAGCAAACACTGGATGTGAAATCCATC |
| K320Q-R | GATTTCACATCCAGTGTTTGCTTGATGAAGTCGGTGTTG |
| K320R-F | ACCGACTTCATCAAGCGTACACTGGATGTGAAATCCATC |
| K320R-R | GATTTCACATCCAGTGTACGCTTGATGAAGTCGGTGTTG |
| K320S-F | ACCGACTTCATCAAGTCAACACTGGATGTGAAATCCATC |
| K320S-R | GATTTCACATCCAGTGTTGACTTGATGAAGTCGGTGTTG |
| K320T-F | ACCGACTTCATCAAGACAACACTGGATGTGAAATCCATC |
| K320T-R | GATTTCACATCCAGTGTTGTCTTGATGAAGTCGGTGTTG |
| K320V-F | ACCGACTTCATCAAGGTAACACTGGATGTGAAATCCATC |
| K320V-R | GATTTCACATCCAGTGTTACCTTGATGAAGTCGGTGTTG |
| K320W-F | ACCGACTTCATCAAGTGGACACTGGATGTGAAATCCATC |
| K320W-R | GATTTCACATCCAGTGTCCACTTGATGAAGTCGGTGTTG |
| K320Y-F | ACCGACTTCATCAAGTACACACTGGATGTGAAATCCATC |
| K320Y-R | GATTTCACATCCAGTGTGTACTTGATGAAGTCGGTGTTG |

Illustrative CadA Nucleic Acid an Polypeptide Sequences:

*Escherichia coli* cadA nucleic acid sequence

SEQ ID NO: 1

ATGAACGTTATTGCAATATTGAATCACATGGGGGTTTATTTTAAAGAAGAACCCA

TCCGTGAACTTCATCGCGCGCTTGAACGTCTGAACTTCCAGATTGTTTACCCGAA

CGACCGTGACGACTTATTAAAACTGATCGAAAACAATGCGCGTCTGTGCGGCGTT

ATTTTTGACTGGGATAAATATAATCTCGAGCTGTGCGAAGAAATTAGCAAAATGA

ACGAGAACCTGCCGTTGTACGCGTTCGCTAATACGTATTCCACTCTCGATGTAAG

CCTGAATGACCTGCGTTTACAGATTAGCTTCTTTGAATATGCGCTGGGTGCTGCT

GAAGATATTGCTAATAAGATCAAGCAGACCACTGACGAATATATCAACACTATT

CTGCCTCCGCTGACTAAAGCACTGTTTAAATATGTTCGTGAAGGTAAATATACTT

TCTGTACTCCTGGTCACATGGGCGGTACTGCATTCCAGAAAAGCCCGGTAGGTAG

CCTGTTCTATGATTTCTTTGGTCCGAATACCATGAAATCTGATATTTCCATTTCAG

TATCTGAACTGGGTTCTCTGCTGGATCACAGTGGTCCACACAAAGAAGCAGAAC

AGTATATCGCTCGCGTCTTTAACGCAGACCGCAGCTACATGGTGACCAACGGTAC

TTCCACTGCGAACAAAATTGTTGGTATGTACTCTGCTCCAGCAGGCAGCACCATT

CTGATTGACCGTAACTGCCACAAATCGCTGACCCACCTGATGATGATGAGCGATG

TTACGCCAATCTATTTCCGCCCGACCCGTAACGCTTACGGTATTCTTGGTGGTATC

CCACAGAGTGAATTCCAGCACGCTACCATTGCTAAGCGCGTGAAAGAAACACCA

AACGCAACCTGGCCGGTACATGCTGTAATTACCAACTCTACCTATGATGGTCTGC

TGTACAACACCGACTTCATCAAGAAAACACTGGATGTGAAATCCATCCACTTTGA

CTCCGCGTGGGTGCCTTACACCAACTTCTCACCGATTTACGAAGGTAAATGCGGT

ATGAGCGGTGGCCGTGTAGAAGGGAAAGTGATTTACGAAACCCAGTCCACTCAC

AAACTGCTGGCGGCGTTCTCTCAGGCTTCCATGATCCACGTTAAAGGTGACGTAA

ACGAAGAAACCTTTAACGAAGCCTACATGATGCACACCACCACTTCTCCGCACTA

CGGTATCGTGGCGTCCACTGAAACCGCTGCGGCGATGATGAAAGGCAATGCAGG

TAAGCGTCTGATCAACGGTTCTATTGAACGTGCGATCAAATTCCGTAAAGAGATC

AAACGTCTGAGAACGGAATCTGATGGCTGGTTCTTTGATGTATGGCAGCCGGATC

ATATCGATACGACTGAATGCTGGCCGCTGCGTTCTGACAGCACCTGGCACGGCTT

CAAAAACATCGATAACGAGCACATGTATCTTGACCCGATCAAAGTCACCCTGCT

GACTCCGGGGATGGAAAAAGACGGCACCATGAGCGACTTTGGTATTCCGGCCAG

CATCGTGGCGAAATACCTCGACGAACATGGCATCGTTGTTGAGAAAACCGGTCC

GTATAACCTGCTGTTCCTGTTCAGCATCGGTATCGATAAGACCAAAGCACTGAGC

CTGCTGCGTGCTCTGACTGACTTTAAACGTGCGTTCGACCTGAACCTGCGTGTGA

AAAACATGCTGCCGTCTCTGTATCGTGAAGATCCTGAATTCTATGAAAACATGCG

TATTCAGGAACTGGCTCAGAATATCCACAAACTGATTGTTCACCACAATCTGCCG

GATCTGATGTATCGCGCATTTGAAGTGCTGCCGACGATGGTAATGACTCCGTATG

CTGCATTCCAGAAAGAGCTGCACGGTATGACCGAAGAAGTTTACCTCGACGAAA

TGGTAGGTCGTATTAACGCCAATATGATCCTTCCGTACCCGCCGGGAGTTCCTCT

GGTAATGCCGGGTGAAATGATCACCGAAGAAAGCCGTCCGGTTCTGGAGTTCCT

```
GCAGATGCTGTGTGAAATCGGCGCTCACTATCCGGGCTTTGAAACCGATATTCAC

GGTGCATACCGTCAGGCTGATGGCCGCTATACCGTTAAGGTATTGAAAGAAGAA

AGCAAAAAATAA
```

E. coli CadA polypeptide sequence The lysine residues at
positions 320 and 325 are underlined and indicated in bold.
SEQ ID NO: 2

```
MNVIAILNHMGVYFKEEPIRELHRALERLNFQIVYPNDRDDLLKLIENNARLCGVIF

DWDKYNLELCEEISKMNENLPLYAFANTYSTLDVSLNDLRLQISFFEYALGAAEDIA

NKIKQTTDEYINTILPPLTKALFKYVREGKYTFCTPGHMGGTAFQKSPVGSLFYDFF

GPNTMKSDISISVSELGSLLDHSGPHKEAEQYIARVFNADRSYMVTNGTSTANKIVG

MYSAPAGSTILIDRNCHKSLTHLMMMSDVTPIYFRPTRNAYGILGGIPQSEFQHATI

AKRVKETPNATWPVHAVITNSTYDGLLYNTDFIKKTLDVKSIHFDSAWVPYTNFSPI

YEGKCGMSGGRVEGKVIYETQSTHKLLAAFSQASMIHVKGDVNEETFNEAYMMHTTT

SPHYGIVASTETAAAMMKGNAGKRLINGSIERAIKFRKEIKRLRTESDGWFFDVWQP

DHIDTTECWPLRSDSTWHGFKNIDNEHMYLDPIKVTLLTPGMEKDGTMSDFGIPASI

VAKYLDEHGIVVEKTGPYNLLFLFSIGIDKTKALSLLRALTDFKRAFDLNLRVKNML

PSLYREDPEFYENMRIQELAQNIHKLIVHHNLPDLMYRAFEVLPTMVMTPYAAFQKE

LHGMTEEVYLDEMVGRINANMILPYPPGVPLVMPGEMITEESRPVLEFLQMLCEIGA

HYPGFETDIHGAYRQADGRYTVKVLKEESKK
```

Polypeptide from Klebsiella homologous to E. coli CadA
SEQ ID NO: 3

```
MNVIAIMNHMGVYFKEEPIRELHRALERLDFRIVYPNDRDDLLKLIENNSRLCGVIF

DWDKYNLELCEEISKMNEYMPLYAFANTYSTLDVSLNDLRMQVRFFEYALGAAEDIA

NKIKQNTDEYIDTILPPLTKALFKYVREGKYTFCTPGHMGGTAFQKSPVGSIFYDFF

GPNTMKSDISISVSELGSLLDHSGPHKEAEEYIARVFNAERSYMVTNGTSTANKIVG

MYSAPAGSTVLIDRNCHKSLTHLMMMSDITPIYFRPTRNAYGILGGIPQSEFQHATI

AKRVKETPNATWPVHAVITNSTYDGLLYNTDFIKKTLDVKSIHFDSAWVPYTNFSPI

YEGKCGMSGGRVEGKVIYETQSTHKLLAAFSQASMIHVKGDVNEETFNEAYMMHTTT

SPHYGIVASTETAAAMMKGNAGKRLIDGSIERSIKFRKEIKRLKGESDGWFFDVWQP

EHIDGPECWPLRSDSAWHGFKNIDNEHMYLDPIKVTLLTPGMKKDGTMDDFGIPASI

VAKYLDEHGIVVEKTGPYNLLFLFSIGIDKTKALSLLRALTDFKRAFDLNLRVKNML

PSLYREDPEFYENMRIQDLAQNIHKLIEHHNLPDLMFRAFEVLPSMVMTPYAAFQKE

LHGQTEEVYLEEMVGRVNANMILPYPPGVPLVMPGEMITEESRPVLEFLQMLCEIGA

HYPGFETDIHGAYRQADGRYTVKVLKEENNK
```

Polypeptide from Enterobacteriaceae homologous to E. coli CadA
SEQ ID NO: 4

```
MNVIAIMNHMGVYFKEEPIRELHRALERLDFRIVYPNDRDDLLKLIENNSRLCGVIF

DWDKYNLELCEEISKMNEYMPLYAFANTYSTLDVSLNDLRMQVRFFEYALGAAEDIA

NKIKQNTDEYIDTILPPLTKALFKYVREGKYTFCTPGHMGGTAFQKSPVGSIFYDFF

GSNTMKSDISISVSELGSLLDHSGPHKEAEEYIARVFNAERSYMVTNGTSTANKIVG

MYSAPAGSTVLIDRNCHKSLTHLMMMSDITPIYFRPTRNAYGILGGIPQSEFQHATI

AKRVKETPNATWPVHAVITNSTYDGLLYNTDFIKKTLDVKSIHFDSAWVPYTNFSPI

YEGKCGMSGGRVEGKVIYETQSTHKLLAAFSQASMIHVKGDVNEETFNEAYMMHTTT

SPHYGIVASTETAAAMMKGNAGKRLIDGSIERSIKFRKEIKRLKGESDGWFFDVWQP
```

-continued

EHIDGPECWPLRSDSAWHGFKNIDNEHMYLDPIKVTLLTPGMKKDGTMDDFGIPASI

VAKYLDEHGIVVEKTGPYNLLFLFSIGIDKTKALSLLRALTDFKRAFDLNLRVKNML

PSLYREDPEFYENMRIQDLAQNIHKLIEHHNLPDLMFRAFEVLPSMVMTPYAAFQKE

LHGQTEEVYLEEMVGRVNANMILPYPPGVPLVMPGEMITEESRPVLEFLQMLCEIGA

HYPGFETDIHGAYRQADGRYTVKVLKEENNK

Polypeptide from *Salmonella enterica* homologous to *E. coli* CadA
SEQ ID NO: 5

MNVIAIMNHMGVYFKEEPIRELHRALEGLNFRIVYPNDREDLLKLIENNSRLCGVIF

DWDKYNLELCEEISKLNEYMPLYAFANSYSTLDVSLNDLRMQVRFFEYALGAATDIA

AKIRQNTDEYIDNILPPLTKALFKYVREGKYTFCTPGHMGGTAFQKSPVGSIFYDFF

GPNTMKSDISISVSELGSLLDHSGPHKEAEEYIARVFNAERSYMVTNGTSTANKIVG

MYSAPAGSTVLIDRNCHKSLTHLMMMSDITPIYFRPTRNAYGILGGIPQSEFQHATI

AKRVKETPNATWPVHAVITNSTYDGLLYNTDYIKKTLDVKSIHFDSAWVPYTNFSPI

YQGKCGMSGDRVEGKIIYETQSTHKLLAAFSQASMIFIVKGDINEETFNEAYMMHTT

TSPHYGIVASTETAAAMMKGNAGKRLINGSIERAIKFRKEIKRLKSESDGWFFDVWQ

PEHIDGAECWPLRSDSAWHGFKNIDNEHMYLDPIKVTILTPGMKKDGTMDEFGIPAS

LVAKYLDERGIIVEKTGPYNLLFLFSIGIDKTKALSLLRALTEFKRAFDLNLRVKNI

LPALYREAPEFYENMRIQELAQNIHKLVEHHNLPDLMYRAFEVLPKMVMTPYTAFQK

ELHGETEEVYLEEMVGRVNANMILPYPPGVPLVMPGEMITEESRPVLEFLQMLCEIG

AHYPGFETDIHGAYRQADGRYTVKVLKENTK

---

What is claimed is:

1. A CadA variant polypeptide comprising at least one amino acid substitution at a lysine residue in a region corresponding to amino acids 276 to 509 as determined with reference to SEQ ID NO: 2, wherein the lysine residue occurs at the surface of the CadA variant polypeptide with the side chain oriented towards the external environment in a segment of the CadA variant polypeptide that lacks a defined secondary structure; and wherein the CadA variant polypeptide has at least 99% identity to any one of SEQ ID NOs: 2 to 5, wherein the substitution is at least at one of positions K320 and K325, wherein the substitution at position K320 is K320A/C/E/G/H/I/L/M/S/V/Y, and wherein the substitution at position K325 is K325C, wherein the lysine decarboxylase activity of the CadA variant polypeptide is improved compared to that of a wildtype CadA of one of SEQ ID NOs: 2 to 5.

2. The CadA variant polypeptide of claim 1, where the amino acid substitution is K320C/E/G/L/V/Y.

3. The CadA variant polypeptide of claim 1, wherein the CadA variant polypeptide, further comprises at least one of substitutions at E291 and E355.

4. The CadA variant polypeptide of claim 3, wherein the CadA variant polypeptide further comprises an substitution at E355.

5. The CadA variant polypeptide of claim 1, wherein the CadA variant polypeptide comprises substitutions E355C and K320C.

6. The CadA variant polypeptide of claim 1, which is immobilized to a solid support.

7. A polynucleotide comprising a nucleic acid sequence encoding a CadA variant polypeptide of claim 1.

8. An expression vector comprising a polynucleotide of claim 7.

9. The expression vector of claim 8, wherein the expression vector is selected from the group consisting of M1 3 phage or lambda phage, plasmid vector pUC18, plasmid vector pUC19, and plasmids derived therefrom.

10. A genetically modified host cell comprising a CadA variant polypeptide of claim 1.

11. The genetically modified host cell of claim 10, wherein the host cell is genetically modified to over express one or more lysine biosynthesis polypeptides.

12. The genetically modified host cell of claim 10, comprising an expression vector comprising a polynucleotide encoding a CadA variant polypeptide comprising at least one amino acid substitution at a lysine residue in a region corresponding to amino acids 276 to 509 as determined with reference to SEQ ID NO: 2, wherein the lysine residue occurs at the surface of the CadA variant polypeptide with the side chain oriented towards the external environment in a segment of the CadA variant polypeptide that lacks a defined secondary structure; and wherein the CadA variant polypeptide has at least 99% identity to any one of SEQ ID NOs: 2 to 5, wherein the substitution is at least at one of positions K320 and K325, wherein the substitution at position K320 is K320A/C/E/G/H/I/L/M/S/V/Y, and wherein the substitution at position K325 is K325C, wherein the lysine decarboxylase activity of the CadA variant polypeptide is improved compared to that of a wildtype CadA of one of SEQ ID NOs: 2 to 5.

13. The genetically modified host cell of claim 10, comprising the polynucleotide comprising a nucleic acid sequence encoding a CadA variant polypeptide comprising at least one amino acid substitution at a lysine residue in a region corresponding to amino acids 276 to 509 as determined with reference to SEQ ID NO: 2, wherein the lysine residue occurs at the surface of the CadA variant polypeptide with the side chain oriented towards the external environment in a segment of the CadA variant polypeptide that lacks a defined secondary structure; and wherein the CadA variant polypeptide has at least 99% identity to any one of SEQ ID NOs: 2 to 5, wherein the substitution is at least at one of positions K320 and K325, wherein the substitution at position K320 is K320A/C/E/G/H/I/L/M/S/V/Y, and wherein the substitution at position K325 is K325C, wherein the lysine decarboxylase activity of the CadA variant polypeptide is improved compared to that of a wildtype CadA of one of SEQ ID NOs: 2 to 5 wherein the nucleic acid sequence encoding the product is integrated into the host cell chromosome.

14. The genetically modified host cell of claim 10, wherein the host cell is a bacterium.

15. The genetically modified host cell of claim 14, wherein the host cell is from the genus *Escherichia, Hafnia,* or *Corynebacteria.*

16. The genetically modified host cell of claim 14, wherein the host cell is selected from the group consisting of *Escherichia coli, Hafnia alvei,* and *Corynebacterium glutamicum.*

17. A method of producing cadaverine, the method comprising culturing the genetically modified host cell of claim 10, under conditions in which the CadA variant polypeptide is expressed.

* * * * *

SEQUENCE LISTING

<160> NUMBER OF SEQ ID NOS: 51

<210> SEQ ID NO 1
<211> LENGTH: 2148
<212> TYPE: DNA
<213> ORGANISM: Escherichia coli

<400> SEQUENCE: 1

```
atgaacgtta ttgcaatatt gaatcacatg ggggtttatt ttaaagaaga acccatccgt      60
gaacttcatc gcgcgcttga acgtctgaac ttccagattg tttacccgaa cgaccgtgac     120
gacttattaa aactgatcga aaacaatgcg cgtctgtgcg gcgttatttt tgactgggat     180
aaatataatc tcgagctgtg cgaagaaatt agcaaaatga cgagaaacct gccgttgtac     240
gcgttcgcta atacgtattc cactctcgat gtaagcctga tgacctgcg tttacagatt      300 agcttctttg aatatgcgct gggtgctgct gaagatattg ctaataagat caagcagacc     360
actgacgaat atatcaacac tattctgcct ccgctgacta agcactgtt taaatatgtt      420 cgtgaaggta aatatacttt ctgtactcct ggtcacatgg gcggtactgc attccagaaa     480
agcccggtag gtagcctgtt ctatgatttc tttggtccga ataccatgaa atctgatatt     540
tccatttcag tatctgaact gggttctctg ctggatcaca gtggtccaca caagaagca     600 gaacagtata tcgctcgcgt ctttaacgca gaccgcagct acatggtgac caacggtact     660
tccactgcga acaaaattgt tggtatgtac tctgctccag caggcagcac cattctgatt     720
gaccgtaact gccacaaatc gctgacccac ctgatgatga tgagcgatgt tacgccaatc     780
tatttccgcc cgacccgtaa cgcttacggt attcttggtg gtatcccaca gagtgaattc     840
```

```
cagcacgcta ccattgctaa gcgcgtgaaa gaaacaccaa acgcaacctg gccggtacat      900
gctgtaatta ccaactctac ctatgatggt ctgctgtaca acaccgactt catcaagaaa      960
acactggatg tgaaatccat ccactttgac tccgcgtggg tgccttacac caacttctca     1020
ccgatttacg aaggtaaatg cggtatgagc ggtggccgtg tagaagggaa agtgatttac     1080
gaaacccagt ccactcacaa actgctggcg gcgttctctc aggcttccat gatccacgtt     1140
aaaggtgacg taaacgaaga aacctttaac gaagcctaca tgatgcacac caccacttct     1200
ccgcactacg gtatcgtggc gtccactgaa accgctgcgg cgatgatgaa aggcaatgca     1260
ggtaagcgtc tgatcaacgg ttctattgaa cgtgcgatca aattccgtaa agagatcaaa     1320
cgtctgagaa cggaatctga tggctggttc tttgatgtat ggcagccgga tcatatcgat     1380
acgactgaat gctggccgct gcgttctgac agcacctggc acggcttcaa aaacatcgat     1440
aacgagcaca tgtatcttga cccgatcaaa gtcaccctgc tgactccggg atggaaaaaa     1500
gacggcacca tgagcgactt ggtattccg gccagcatcg tggcgaaata cctcgacgaa     1560
catggcatcg ttgttgagaa accggtccg tataacctgc tgttcctgtt cagcatcggt     1620
atcgataaga ccaaagcact gagcctgctg cgtgctctga ctgactttaa acgtgcgttc     1680
gacctgaacc tgcgtgtgaa aaacatgctg ccgtctctgt atcgtgaaga tcctgaattc     1740
tatgaaaaca tgcgtattca ggaactggct cagaatatcc acaaactgat tgttcaccac     1800
aatctgccgg atctgatgta tcgcgcattt gaagtgctgc cgacgatggt aatgactccg     1860
tatgctgcat tccagaaaga gctgcacggt atgaccgaag aagtttacct cgacgaaatg     1920
gtaggtcgta ttaacgccaa tatgatcctt ccgtacccgc cgggagttcc tctggtaatg     1980
ccgggtgaaa tgatcaccga agaaagccgt ccggttctgg agttcctgca gatgctgtgt     2040
gaaatcggcg ctcactatcc gggctttgaa accgatattc acggtgcata ccgtcaggct     2100
gatggccgct ataccgttaa ggtattgaaa gaagaaagca aaaaataa                  2148
```

<210> SEQ ID NO 2  
<211> LENGTH: 715  
<212> TYPE: PRT  
<213> ORGANISM: Escherichia coli

<400> SEQUENCE: 2

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

```
Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
            165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
            245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
            290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
            325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
            405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
            485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560
```

```
Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 3
<211> LENGTH: 715
<212> TYPE: PRT
<213> ORGANISM: Klebsiella

<400> SEQUENCE: 3

Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

Ile Val Tyr Pro Asn Asp Arg Asp Asp Leu Leu Lys Leu Ile Glu Asn
        35                  40                  45

Asn Ser Arg Leu Cys Gly Val Ile Phe Asp Trp Asp Lys Tyr Asn Leu
    50                  55                  60

Glu Leu Cys Glu Glu Ile Ser Lys Met Asn Glu Tyr Met Pro Leu Tyr
65                  70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp
            100                 105                 110

Ile Ala Asn Lys Ile Lys Gln Asn Thr Asp Glu Tyr Ile Asp Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Glu Tyr Ile Ala Arg Val Phe
        195                 200                 205

Asn Ala Glu Arg Ser Tyr Met Val Thr Asn Gly Thr Ser Thr Ala Asn
    210                 215                 220
```

```
Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
        290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asp Gly Ser Ile Glu Arg Ser
            420                 425                 430

Ile Lys Phe Arg Lys Glu Ile Lys Arg Leu Lys Gly Glu Ser Asp Gly
            435                 440                 445

Trp Phe Phe Asp Val Trp Gln Pro Glu His Ile Asp Gly Pro Glu Cys
        450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Lys Lys Asp Gly Thr Met Asp Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Asp Leu Ala Gln Asn
            580                 585                 590

Ile His Lys Leu Ile Glu His His Asn Leu Pro Asp Leu Met Phe Arg
            595                 600                 605

Ala Phe Glu Val Leu Pro Ser Met Val Met Thr Pro Tyr Ala Ala Phe
        610                 615                 620

Gln Lys Glu Leu His Gly Gln Thr Glu Glu Val Tyr Leu Glu Glu Met
625                 630                 635                 640
```

```
Val Gly Arg Val Asn Ala Asn Met Ile Leu Pro Tyr Pro Pro Gly Val
            645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
            690                 695                 700

Thr Val Lys Val Leu Lys Glu Glu Asn Asn Lys
705                 710                 715

<210> SEQ ID NO 4
<211> LENGTH: 715
<212> TYPE: PRT
<213> ORGANISM: Enterobacteriaceae

<400> SEQUENCE: 4

Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

Ile Val Tyr Pro Asn Asp Arg Asp Asp Leu Leu Lys Leu Ile Glu Asn
        35                  40                  45

Asn Ser Arg Leu Cys Gly Val Ile Phe Asp Trp Asp Lys Tyr Asn Leu
50                  55                  60

Glu Leu Cys Glu Glu Ile Ser Lys Met Asn Glu Tyr Met Pro Leu Tyr
65                  70                  75                  80

Ala Phe Ala Asn Thr Tyr Ser Thr Leu Asp Val Ser Leu Asn Asp Leu
                85                  90                  95

Arg Met Gln Val Arg Phe Phe Glu Tyr Ala Leu Gly Ala Ala Glu Asp
            100                 105                 110

Ile Ala Asn Lys Ile Lys Gln Asn Thr Asp Glu Tyr Ile Asp Thr Ile
        115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Ser Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Glu Tyr Ile Ala Arg Val Phe
        195                 200                 205

Asn Ala Glu Arg Ser Tyr Met Val Thr Asn Gly Thr Ser Thr Ala Asn
210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300
```

```
Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
            325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
            405                 410                 415

Lys Gly Asn Ala Gly Lys Arg Leu Ile Asp Gly Ser Ile Glu Arg Ser
            420                 425                 430

Ile Lys Phe Arg Lys Glu Ile Lys Arg Leu Lys Gly Glu Ser Asp Gly
            435                 440                 445

Trp Phe Phe Asp Val Trp Gln Pro Glu His Ile Asp Gly Pro Glu Cys
450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Leu Thr Pro
            485                 490                 495

Gly Met Lys Lys Asp Gly Thr Met Asp Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
            565                 570                 575

Asp Pro Glu Phe Tyr Glu Asn Met Arg Ile Gln Asp Leu Ala Gln Asn
            580                 585                 590

Ile His Lys Leu Ile Glu His His Asn Leu Pro Asp Leu Met Phe Arg
            595                 600                 605

Ala Phe Glu Val Leu Pro Ser Met Val Met Thr Pro Tyr Ala Ala Phe
610                 615                 620

Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
            645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
            690                 695                 700

Thr Val Lys Val Leu Lys Glu Glu Asn Asn Lys
705                 710                 715
```

<210> SEQ ID NO 5
<211> LENGTH: 714
<212> TYPE: PRT
<213> ORGANISM: Salmonella enterica

<400> SEQUENCE: 5

```
Met Asn Val Ile Ala Ile Met Asn His Met Gly Val Tyr Phe Lys Glu
1               5                   10                  15

Glu Pro Ile Arg Glu Leu His Arg Ala Leu Glu Gly Leu Asn Phe Arg
            20                  25                  30

Ile Val Tyr Pro Asn Asp Arg Glu Asp Leu Leu Lys Leu Ile Glu Asn
        35                  40                  45

Asn Ser Arg Leu Cys Gly Val Ile Phe Asp Trp Asp Lys Tyr Asn Leu
    50                  55                  60

Glu Leu Cys Glu Glu Ile Ser Lys Leu Asn Glu Tyr Met Pro Leu Tyr
65                  70                  75                  80

Ala Phe Ala Asn Ser Tyr Ser Thr Leu Asp Val Ser Leu Asn Asp Leu
                85                  90                  95

Arg Met Gln Val Arg Phe Phe Glu Tyr Ala Leu Gly Ala Ala Thr Asp
            100                 105                 110

Ile Ala Ala Lys Ile Arg Gln Asn Thr Asp Glu Tyr Ile Asp Asn Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Glu Tyr Ile Ala Arg Val Phe
        195                 200                 205

Asn Ala Glu Arg Ser Tyr Met Val Thr Asn Gly Thr Ser Thr Ala Asn
    210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Tyr Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Gln Gly Lys Cys Gly Met Ser Gly Asp
            340                 345                 350

Arg Val Glu Gly Lys Ile Ile Tyr Glu Thr Gln Ser Thr His Lys Leu
        355                 360                 365

Leu Ala Ala Phe Ser Gln Ala Ser Met Ile His Val Lys Gly Asp Ile
    370                 375                 380
```

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
            405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Lys Ser Glu Ser Asp Gly
            435                 440                 445

Trp Phe Phe Asp Val Trp Gln Pro Glu His Ile Asp Gly Ala Glu Cys
            450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Ile Leu Thr Pro
                485                 490                 495

Gly Met Lys Lys Asp Gly Thr Met Asp Glu Phe Gly Ile Pro Ala Ser
                500                 505                 510

Leu Val Ala Lys Tyr Leu Asp Glu Arg Gly Ile Ile Val Glu Lys Thr
            515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Glu Phe Lys Arg Ala Phe
545                 550                 555                 560

Asp Leu Asn Leu Arg Val Lys Asn Ile Leu Pro Ala Leu Tyr Arg Glu
                565                 570                 575

Ala Pro Glu Phe Tyr Glu Asn Met Arg Ile Gln Glu Leu Ala Gln Asn
            580                 585                 590

Ile His Lys Leu Val Glu His His Asn Leu Pro Asp Leu Met Tyr Arg
            595                 600                 605

Ala Phe Glu Val Leu Pro Lys Met Val Met Thr Pro Tyr Thr Ala Phe
            610                 615                 620

Gln Lys Glu Leu His Gly Glu Thr Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
            690                 695                 700

Thr Val Lys Val Leu Lys Glu Asn Thr Lys
705                 710

<210> SEQ ID NO 6
<211> LENGTH: 52
<212> TYPE: DNA
<213> ORGANISM: Artificial Sequence
<220> FEATURE:
<223> OTHER INFORMATION: Primer cadA-F

<400> SEQUENCE: 6
ggcgagctca cacaggaaac agaccatgaa cgttattgca atattgaatc ac        52

<210> SEQ ID NO 7
<211> LENGTH: 28

<212> TYPE: DNA
<213> ORGANISM: Artificial Sequence
<220> FEATURE:
<223> OTHER INFORMATION: Primer cadA-R

<400> SEQUENCE: 7
ggctctagac cacttccctt gtacgagc                                28

<210> SEQ ID NO 8
<211> LENGTH: 44
<212> TYPE: DNA
<213> ORGANISM: Artificial Sequence
<220> FEATURE:
<223> OTHER INFORMATION: Primer cadA-F2

<400> SEQUENCE: 8
atttcacaca ggaaacagct atgaacgtta ttgcaatatt gaat              44

<210> SEQ ID NO 9
<211> LENGTH: 20
<212> TYPE: DNA
<213> ORGANISM: Artificial Sequence
<220> FEATURE:
<223> OTHER INFORMATION: Primer cadA-R2

<400> SEQUENCE: 9
agctgtttcc tgtgtgaaat                                         20

<210> SEQ ID NO 10
<211> LENGTH: 39
<212> TYPE: DNA
<213> ORGANISM: Artificial Sequence
<220> FEATURE:
<223> OTHER INFORMATION: Primer K320A-F

<400> SEQUENCE: 10
accgacttca tcaaggcaac actggatgtg aaatccatc                    39

<210> SEQ ID NO 11
<211> LENGTH: 39
<212> TYPE: DNA
<213> ORGANISM: Artificial Sequence
<220> FEATURE:
<223> OTHER INFORMATION: Primer K320A-R

<400> SEQUENCE: 11
gatttcacat ccagtgttgc cttgatgaag tcggtgttg                    39

<210> SEQ ID NO 12
<211> LENGTH: 39
<212> TYPE: DNA
<213> ORGANISM: Artificial Sequence
<220> FEATURE:
<223> OTHER INFORMATION: Primer K320C-F

<400> SEQUENCE: 12
accgacttca tcaagtgcac actggatgtg aaatccatc                    39

<210> SEQ ID NO 13
<211> LENGTH: 39
<212> TYPE: DNA
<213> ORGANISM: Artificial Sequence
<220> FEATURE:
<223> OTHER INFORMATION: Primer K320C-R

```
<400> SEQUENCE: 13
gatttcacat ccagtgtgca cttgatgaag tcggtgttg                                 39

<210> SEQ ID NO 14
<211> LENGTH: 39
<212> TYPE: DNA
<213> ORGANISM: Artificial Sequence
<220> FEATURE:
<223> OTHER INFORMATION: Primer K320D-F

<400> SEQUENCE: 14
accgacttca tcaaggacac actggatgtg aaatccatc                                 39

<210> SEQ ID NO 15
<211> LENGTH: 39
<212> TYPE: DNA
<213> ORGANISM: Artificial Sequence
<220> FEATURE:
<223> OTHER INFORMATION: Primer K320D-R

<400> SEQUENCE: 15
gatttcacat ccagtgtgtc cttgatgaag tcggtgttg                                 39

<210> SEQ ID NO 16
<211> LENGTH: 39
<212> TYPE: DNA
<213> ORGANISM: Artificial Sequence
<220> FEATURE:
<223> OTHER INFORMATION: Primer K320E-F

<400> SEQUENCE: 16
accgacttca tcaaggaaac actggatgtg aaatccatc                                 39

<210> SEQ ID NO 17
<211> LENGTH: 39
<212> TYPE: DNA
<213> ORGANISM: Artificial Sequence
<220> FEATURE:
<223> OTHER INFORMATION: Primer K320E-R

<400> SEQUENCE: 17
gatttcacat ccagtgtttc cttgatgaag tcggtgttg                                 39

<210> SEQ ID NO 18
<211> LENGTH: 39
<212> TYPE: DNA
<213> ORGANISM: Artificial Sequence
<220> FEATURE:
<223> OTHER INFORMATION: Primer K320F-F

<400> SEQUENCE: 18
accgacttca tcaagttcac actggatgtg aaatccatc                                 39

<210> SEQ ID NO 19
<211> LENGTH: 39
<212> TYPE: DNA
<213> ORGANISM: Artificial Sequence
<220> FEATURE:
<223> OTHER INFORMATION: Primer K320F-R

<400> SEQUENCE: 19
gatttcacat ccagtgtgaa cttgatgaag tcggtgttg                                 39

<210> SEQ ID NO 20
```

<210> SEQ ID NO 20
<211> LENGTH: 39
<212> TYPE: DNA
<213> ORGANISM: Artificial Sequence
<220> FEATURE:
<223> OTHER INFORMATION: Primer K320G-F

<400> SEQUENCE: 20
accgacttca tcaagggaac actggatgtg aaatccatc          39

<210> SEQ ID NO 21
<211> LENGTH: 39
<212> TYPE: DNA
<213> ORGANISM: Artificial Sequence
<220> FEATURE:
<223> OTHER INFORMATION: Primer K320G-R

<400> SEQUENCE: 21
gatttcacat ccagtgttcc cttgatgaag tcggtgttg          39

<210> SEQ ID NO 22
<211> LENGTH: 39
<212> TYPE: DNA
<213> ORGANISM: Artificial Sequence
<220> FEATURE:
<223> OTHER INFORMATION: Primer K320H-F

<400> SEQUENCE: 22
accgacttca tcaagcatac actggatgtg aaatccatc          39

<210> SEQ ID NO 23
<211> LENGTH: 39
<212> TYPE: DNA
<213> ORGANISM: Artificial Sequence
<220> FEATURE:
<223> OTHER INFORMATION: Primer K320H-R

<400> SEQUENCE: 23
gatttcacat ccagtgtatg cttgatgaag tcggtgttg          39

<210> SEQ ID NO 24
<211> LENGTH: 39
<212> TYPE: DNA
<213> ORGANISM: Artificial Sequence
<220> FEATURE:
<223> OTHER INFORMATION: Primer K320I-F

<400> SEQUENCE: 24
accgacttca tcaagatcac actggatgtg aaatccatc          39

<210> SEQ ID NO 25
<211> LENGTH: 39
<212> TYPE: DNA
<213> ORGANISM: Artificial Sequence
<220> FEATURE:
<223> OTHER INFORMATION: Primer K320I-R

<400> SEQUENCE: 25
gatttcacat ccagtgtgat cttgatgaag tcggtgttg          39

<210> SEQ ID NO 26
<211> LENGTH: 39
<212> TYPE: DNA
<213> ORGANISM: Artificial Sequence
<220> FEATURE:
<223> OTHER INFORMATION: Primer K320L-F

<400> SEQUENCE: 26
accgacttca tcaagctgac actggatgtg aaatccatc                                    39

<210> SEQ ID NO 27
<211> LENGTH: 39
<212> TYPE: DNA
<213> ORGANISM: Artificial Sequence
<220> FEATURE:
<223> OTHER INFORMATION: Primer K320L-R

<400> SEQUENCE: 27
gatttcacat ccagtgtcag cttgatgaag tcggtgttg                                    39

<210> SEQ ID NO 28
<211> LENGTH: 39
<212> TYPE: DNA
<213> ORGANISM: Artificial Sequence
<220> FEATURE:
<223> OTHER INFORMATION: Primer K320M-F

<400> SEQUENCE: 28
accgacttca tcaagatgac actggatgtg aaatccatc                                    39

<210> SEQ ID NO 29
<211> LENGTH: 39
<212> TYPE: DNA
<213> ORGANISM: Artificial Sequence
<220> FEATURE:
<223> OTHER INFORMATION: Primer K320M-R

<400> SEQUENCE: 29
gatttcacat ccagtgtcat cttgatgaag tcggtgttg                                    39

<210> SEQ ID NO 30
<211> LENGTH: 39
<212> TYPE: DNA
<213> ORGANISM: Artificial Sequence
<220> FEATURE:
<223> OTHER INFORMATION: Primer K320N-F

<400> SEQUENCE: 30
accgacttca tcaagaacac actggatgtg aaatccatc                                    39

<210> SEQ ID NO 31
<211> LENGTH: 39
<212> TYPE: DNA
<213> ORGANISM: Artificial Sequence
<220> FEATURE:
<223> OTHER INFORMATION: Primer K320N-R

<400> SEQUENCE: 31
gatttcacat ccagtgtgtt cttgatgaag tcggtgttg                                    39

<210> SEQ ID NO 32
<211> LENGTH: 39
<212> TYPE: DNA
<213> ORGANISM: Artificial Sequence
<220> FEATURE:
<223> OTHER INFORMATION: Primer K320P-F

<400> SEQUENCE: 32
accgacttca tcaagccaac actggatgtg aaatccatc                                    39

<210> SEQ ID NO 33

<211> LENGTH: 39
<212> TYPE: DNA
<213> ORGANISM: Artificial Sequence
<220> FEATURE:
<223> OTHER INFORMATION: Primer K320P-R

<400> SEQUENCE: 33
gatttcacat ccagtgttgg cttgatgaag tcggtgttg          39

<210> SEQ ID NO 34
<211> LENGTH: 39
<212> TYPE: DNA
<213> ORGANISM: Artificial Sequence
<220> FEATURE:
<223> OTHER INFORMATION: Primer K320Q-F

<400> SEQUENCE: 34
accgacttca tcaagcaaac actggatgtg aaatccatc          39

<210> SEQ ID NO 35
<211> LENGTH: 39
<212> TYPE: DNA
<213> ORGANISM: Artificial Sequence
<220> FEATURE:
<223> OTHER INFORMATION: Primer K320Q-R

<400> SEQUENCE: 35
gatttcacat ccagtgtttg cttgatgaag tcggtgttg          39

<210> SEQ ID NO 36
<211> LENGTH: 39
<212> TYPE: DNA
<213> ORGANISM: Artificial Sequence
<220> FEATURE:
<223> OTHER INFORMATION: Primer K320R-F

<400> SEQUENCE: 36
accgacttca tcaagcgtac actggatgtg aaatccatc          39

<210> SEQ ID NO 37
<211> LENGTH: 39
<212> TYPE: DNA
<213> ORGANISM: Artificial Sequence
<220> FEATURE:
<223> OTHER INFORMATION: Primer K320R-R

<400> SEQUENCE: 37
gatttcacat ccagtgtacg cttgatgaag tcggtgttg          39

<210> SEQ ID NO 38
<211> LENGTH: 39
<212> TYPE: DNA
<213> ORGANISM: Artificial Sequence
<220> FEATURE:
<223> OTHER INFORMATION: Primer K320S-F

<400> SEQUENCE: 38
accgacttca tcaagtcaac actggatgtg aaatccatc          39

<210> SEQ ID NO 39
<211> LENGTH: 39
<212> TYPE: DNA
<213> ORGANISM: Artificial Sequence
<220> FEATURE:
<223> OTHER INFORMATION: Primer K320S-R

```
<400> SEQUENCE: 39
gatttcacat ccagtgttga cttgatgaag tcggtgttg                                    39

<210> SEQ ID NO 40
<211> LENGTH: 39
<212> TYPE: DNA
<213> ORGANISM: Artificial Sequence
<220> FEATURE:
<223> OTHER INFORMATION: Primer K320T-F

<400> SEQUENCE: 40
accgacttca tcaagacaac actggatgtg aaatccatc                                    39

<210> SEQ ID NO 41
<211> LENGTH: 39
<212> TYPE: DNA
<213> ORGANISM: Artificial Sequence
<220> FEATURE:
<223> OTHER INFORMATION: Primer K320T-R

<400> SEQUENCE: 41
gatttcacat ccagtgttgt cttgatgaag tcggtgttg                                    39

<210> SEQ ID NO 42
<211> LENGTH: 39
<212> TYPE: DNA
<213> ORGANISM: Artificial Sequence
<220> FEATURE:
<223> OTHER INFORMATION: Primer K320V-F

<400> SEQUENCE: 42
accgacttca tcaaggtaac actggatgtg aaatccatc                                    39

<210> SEQ ID NO 43
<211> LENGTH: 39
<212> TYPE: DNA
<213> ORGANISM: Artificial Sequence
<220> FEATURE:
<223> OTHER INFORMATION: Primer K320V-R

<400> SEQUENCE: 43
gatttcacat ccagtgttac cttgatgaag tcggtgttg                                    39

<210> SEQ ID NO 44
<211> LENGTH: 39
<212> TYPE: DNA
<213> ORGANISM: Artificial Sequence
<220> FEATURE:
<223> OTHER INFORMATION: Primer K320W-F

<400> SEQUENCE: 44
accgacttca tcaagtggac actggatgtg aaatccatc                                    39

<210> SEQ ID NO 45
<211> LENGTH: 39
<212> TYPE: DNA
<213> ORGANISM: Artificial Sequence
<220> FEATURE:
<223> OTHER INFORMATION: Primer K320W-R

<400> SEQUENCE: 45
gatttcacat ccagtgtcca cttgatgaag tcggtgttg                                    39

<210> SEQ ID NO 46
```

<211> LENGTH: 39
<212> TYPE: DNA
<213> ORGANISM: Artificial Sequence
<220> FEATURE:
<223> OTHER INFORMATION: Primer K320Y-F

<400> SEQUENCE: 46
accgacttca tcaagtacac actggatgtg aaatccatc                                39

<210> SEQ ID NO 47
<211> LENGTH: 39
<212> TYPE: DNA
<213> ORGANISM: Artificial Sequence
<220> FEATURE:
<223> OTHER INFORMATION: Primer K320Y-R

<400> SEQUENCE: 47
gatttcacat ccagtgtgta cttgatgaag tcggtgttg                                39

<210> SEQ ID NO 48
<211> LENGTH: 714
<212> TYPE: PRT
<213> ORGANISM: SALMONELLA ENTERICA

<400> SEQUENCE: 48

Met Asn Val Ile Ala Ile Met Asn His Met Gly Val Tyr Phe Lys Glu
1               5                   10                  15

Glu Pro Ile Arg Glu Leu His Arg Ala Leu Gly Leu Asn Phe Arg
            20                  25                  30

Ile Val Tyr Pro Asn Asp Arg Glu Asp Leu Leu Lys Leu Ile Glu Asn
        35                  40                  45

Asn Ser Arg Leu Cys Gly Val Ile Phe Asp Trp Asp Lys Tyr Asn Leu
    50                  55                  60

Glu Leu Cys Glu Glu Ile Ser Lys Leu Asn Glu Tyr Met Pro Leu Tyr
65                  70                  75                  80

Ala Phe Ala Asn Ser Tyr Ser Thr Leu Asp Val Ser Leu Asn Asp Leu
                85                  90                  95

Arg Met Gln Val Arg Phe Phe Glu Tyr Ala Leu Gly Ala Ala Thr Asp
            100                 105                 110

Ile Ala Ala Lys Ile Arg Gln Asn Thr Asp Glu Tyr Ile Asp Asn Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Ile Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Glu Tyr Ile Ala Arg Val Phe
        195                 200                 205

Asn Ala Glu Arg Ser Tyr Met Val Thr Asn Gly Thr Ser Thr Ala Asn
    210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

```
Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Tyr Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Gln Gly Lys Cys Gly Met Ser Gly Asp
            340                 345                 350

Arg Val Glu Gly Lys Ile Ile Tyr Glu Thr Gln Ser Thr His Lys Leu
        355                 360                 365

Leu Ala Ala Phe Ser Gln Ala Ser Met Ile His Val Lys Gly Asp Ile
    370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Lys Ser Glu Ser Asp Gly
        435                 440                 445

Trp Phe Phe Asp Val Trp Gln Pro Glu His Ile Asp Gly Ala Glu Cys
    450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Ile Leu Thr Pro
                485                 490                 495

Gly Met Lys Lys Asp Gly Thr Met Asp Glu Phe Gly Ile Pro Ala Ser
            500                 505                 510

Leu Val Ala Lys Tyr Leu Asp Glu Arg Gly Ile Ile Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Glu Phe Lys Arg Ala Phe
545                 550                 555                 560

Asp Leu Asn Leu Arg Val Lys Asn Ile Leu Pro Ala Leu Tyr Arg Glu
                565                 570                 575

Ala Pro Glu Phe Tyr Glu Asn Met Arg Ile Gln Glu Leu Ala Gln Asn
            580                 585                 590

Ile His Lys Leu Val Glu His His Asn Leu Pro Asp Leu Met Tyr Arg
        595                 600                 605

Ala Phe Glu Val Leu Pro Lys Met Val Met Thr Pro Tyr Thr Ala Phe
    610                 615                 620

Gln Lys Glu Leu His Gly Glu Thr Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670
```

```
Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
            690                 695                 700

Thr Val Lys Val Leu Lys Glu Asn Thr Lys
705                 710

<210> SEQ ID NO 49
<211> LENGTH: 715
<212> TYPE: PRT
<213> ORGANISM: ESCHERICHIA

<400> SEQUENCE: 49

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335
```

-continued

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
        450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 50
<211> LENGTH: 715
<212> TYPE: PRT
<213> ORGANISM: KLEBSIELLA

<400> SEQUENCE: 50

```
Met Asn Val Ile Ala Ile Met Asn His Met Gly Val Tyr Phe Lys Glu
1               5                   10                  15
Glu Pro Ile Arg Glu Leu His Arg Ala Leu Glu Arg Leu Asp Phe Arg
            20                  25                  30
Ile Val Tyr Pro Asn Asp Arg Asp Leu Leu Lys Leu Ile Glu Asn
        35                  40                  45
Asn Ser Arg Leu Cys Gly Val Ile Phe Asp Trp Asp Lys Tyr Asn Leu
    50                  55                  60
Glu Leu Cys Glu Glu Ile Ser Lys Met Asn Glu Tyr Met Pro Leu Tyr
65                  70                  75                  80
Ala Phe Ala Asn Thr Tyr Ser Thr Leu Asp Val Ser Leu Asn Asp Leu
                85                  90                  95
Arg Met Gln Val Arg Phe Phe Glu Tyr Ala Leu Gly Ala Ala Glu Asp
            100                 105                 110
Ile Ala Asn Lys Ile Lys Gln Asn Thr Asp Glu Tyr Ile Asp Thr Ile
        115                 120                 125
Leu Pro Pro Leu Thr Lys Ala Leu Phe Lys Tyr Val Arg Glu Gly Lys
    130                 135                 140
Tyr Thr Phe Cys Thr Pro Gly His Met Gly Gly Thr Ala Phe Gln Lys
145                 150                 155                 160
Ser Pro Val Gly Ser Ile Phe Tyr Asp Phe Phe Gly Pro Asn Thr Met
                165                 170                 175
Lys Ser Asp Ile Ser Ile Ser Val Ser Glu Leu Gly Ser Leu Leu Asp
            180                 185                 190
His Ser Gly Pro His Lys Glu Ala Glu Glu Tyr Ile Ala Arg Val Phe
        195                 200                 205
Asn Ala Glu Arg Ser Tyr Met Val Thr Asn Gly Thr Ser Thr Ala Asn
    210                 215                 220
Lys Ile Val Gly Met Tyr Ser Ala Pro Ala Gly Ser Thr Val Leu Ile
225                 230                 235                 240
Asp Arg Asn Cys His Lys Ser Leu Thr His Leu Met Met Met Ser Asp
                245                 250                 255
Ile Thr Pro Ile Tyr Phe Arg Pro Thr Arg Asn Ala Tyr Gly Ile Leu
            260                 265                 270
Gly Gly Ile Pro Gln Ser Glu Phe Gln His Ala Thr Ile Ala Lys Arg
        275                 280                 285
Val Lys Glu Thr Pro Asn Ala Thr Trp Pro Val His Ala Val Ile Thr
    290                 295                 300
Asn Ser Thr Tyr Asp Gly Leu Leu Tyr Asn Thr Asp Phe Ile Lys Lys
305                 310                 315                 320
Thr Leu Asp Val Lys Ser Ile His Phe Asp Ser Ala Trp Val Pro Tyr
                325                 330                 335
Thr Asn Phe Ser Pro Ile Tyr Glu Gly Lys Cys Gly Met Ser Gly Gly
            340                 345                 350
Arg Val Glu Gly Lys Val Ile Tyr Glu Thr Gln Ser Thr His Lys Leu
        355                 360                 365
Leu Ala Ala Phe Ser Gln Ala Ser Met Ile His Val Lys Gly Asp Val
    370                 375                 380
Asn Glu Glu Thr Phe Asn Glu Ala Tyr Met Met His Thr Thr Thr Ser
385                 390                 395                 400
Pro His Tyr Gly Ile Val Ala Ser Thr Glu Thr Ala Ala Ala Met Met
                405                 410                 415
```

```
Lys Gly Asn Ala Gly Lys Arg Leu Ile Asp Gly Ser Ile Glu Arg Ser
                420                 425                 430

Ile Lys Phe Arg Lys Glu Ile Lys Arg Leu Lys Gly Glu Ser Asp Gly
            435                 440                 445

Trp Phe Asp Val Trp Gln Pro Glu His Ile Asp Gly Pro Glu Cys
        450                 455                 460

Trp Pro Leu Arg Ser Asp Ser Ala Trp His Gly Phe Lys Asn Ile Asp
465                 470                 475                 480

Asn Glu His Met Tyr Leu Asp Pro Ile Lys Val Thr Leu Thr Pro
                485                 490                 495

Gly Met Lys Lys Asp Gly Thr Met Asp Asp Phe Gly Ile Pro Ala Ser
                500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Asp Leu Ala Gln Asn
                580                 585                 590

Ile His Lys Leu Ile Glu His His Asn Leu Pro Asp Leu Met Phe Arg
                595                 600                 605

Ala Phe Glu Val Leu Pro Ser Met Val Met Thr Pro Tyr Ala Ala Phe
        610                 615                 620

Gln Lys Glu Leu His Gly Gln Thr Glu Glu Val Tyr Leu Glu Glu Met
625                 630                 635                 640

Val Gly Arg Val Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
        690                 695                 700

Thr Val Lys Val Leu Lys Glu Glu Asn Asn Lys
705                 710                 715

<210> SEQ ID NO 51
<211> LENGTH: 715
<212> TYPE: PRT
<213> ORGANISM: ENTEROBACTERIAECEAE

<400> SEQUENCE: 51

Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asp Phe Arg
            20                  25                  30

Ile Val Tyr Pro Asn Asp Arg Asp Leu Leu Lys Leu Ile Glu Asn
            35                  40                  45

Asn Ser Arg Leu Cys Gly Val Ile Phe Asp Trp Asp Lys Tyr Asn Leu
50                  55                  60
```

-continued

```
Glu Leu Cys Glu Glu Ile Ser Lys Met Asn Glu Tyr Met Pro Leu Tyr
 65                  70                  75                  80

Ala Phe Ala Asn Thr Tyr Ser Thr Leu Asp Val Ser Leu Asn Asp Leu
                 85                  90                  95

Arg Met Gln Val Arg Phe Phe Gly Tyr Ala Leu Gly Ala Ala Glu Asp
            100                 105                 110

Ile Ala Asn Lys Ile Lys Gln Asn Thr Asp Glu Tyr Ile Asp Thr Ile
        115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Thr Ala Phe Gln Lys
145                 150                 155                 160

Ser Pro Val Gly Ser Ile Phe Tyr Asp Phe Phe Gly Ser Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Glu Tyr Ile Ala Arg Val Phe
        195                 200                 205

Asn Ala Glu Arg Ser Tyr Met Val Thr Asn Gly Thr Ser Thr Ala Asn
210                 215                 220

Lys Ile Val Gly Met Tyr Ser Ala Pro Ala Gly Ser Thr Val Leu Ile
225                 230                 235                 240

Asp Arg Asn Cys His Lys Ser Leu Thr His Leu Met Met Met Ser Asp
                245                 250                 255

Ile Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asp Gly Ser Ile Glu Arg Ser
            420                 425                 430

Ile Lys Phe Arg Lys Glu Ile Lys Arg Leu Lys Gly Glu Ser Asp Gly
        435                 440                 445

Trp Phe Phe Asp Val Trp Gln Pro Glu His Ile Asp Gly Pro Glu Cys
450                 455                 460

Trp Pro Leu Arg Ser Asp Ser Ala Trp His Gly Phe Lys Asn Ile Asp
465                 470                 475                 480
```

-continued

```
Asn Glu His Met Tyr Leu Asp Pro Ile Lys Val Thr Leu Leu Thr Pro
            485             490             495
Gly Met Lys Lys Asp Gly Thr Met Asp Asp Phe Gly Ile Pro Ala Ser
        500             505             510
Ile Val Ala Lys Tyr Leu Asp Glu His Gly Ile Val Val Glu Lys Thr
        515             520             525
Gly Pro Tyr Asn Leu Leu Phe Leu Phe Ser Ile Gly Ile Asp Lys Thr
    530             535             540
Lys Ala Leu Ser Leu Leu Arg Ala Leu Thr Asp Phe Lys Arg Ala Phe
545             550             555             560
Asp Leu Asn Leu Arg Val Lys Asn Met Leu Pro Ser Leu Tyr Arg Glu
            565             570             575
Asp Pro Glu Phe Tyr Glu Asn Met Arg Ile Gln Asp Leu Ala Gln Asn
            580             585             590
Ile His Lys Leu Ile Glu His His Asn Leu Pro Asp Leu Met Phe Arg
        595             600             605
Ala Phe Glu Val Leu Pro Ser Met Val Met Thr Pro Tyr Ala Ala Phe
    610             615             620
Gln Lys Glu Leu His Gly Gln Thr Glu Glu Val Tyr Leu Glu Glu Met
625             630             635             640
Val Gly Arg Val Asn Ala Asn Met Ile Leu Pro Tyr Pro Pro Gly Val
            645             650             655
Pro Leu Val Met Pro Gly Glu Met Ile Thr Glu Glu Ser Arg Pro Val
            660             665             670
Leu Glu Phe Leu Gln Met Leu Cys Glu Ile Gly Ala His Tyr Pro Gly
            675             680             685
Phe Glu Thr Asp Ile His Gly Ala Tyr Arg Gln Ala Asp Gly Arg Tyr
            690             695             700
Thr Val Lys Val Leu Lys Glu Glu Asn Asn Lys
705             710             715
```